(12) United States Patent
Cho et al.

(10) Patent No.: US 7,215,983 B2
(45) Date of Patent: May 8, 2007

(54) BLOOD SUGAR LEVEL MEASURING APPARATUS

(75) Inventors: Ok-Kyung Cho, Schwerte (DE);
Yoon-Ok Kim, Schwerte (DE);
Hideharu Hattori, Odawara (JP);
Hiroshi Mitsumaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 524 days.

(21) Appl. No.: 10/879,780

(22) Filed: Jun. 30, 2004

(65) Prior Publication Data

US 2006/0004268 A1  Jan. 5, 2006

(51) Int. Cl.
*A61B 5/00* (2006.01)
(52) U.S. Cl. .................. 600/316; 600/365; 600/326
(58) Field of Classification Search ................ 600/310, 600/316, 322, 323, 326, 365, 549
See application file for complete search history.

(56) References Cited

U.S. PATENT DOCUMENTS

| | | | |
|---|---|---|---|
| 4,306,569 A | 12/1981 | Weil | |
| 4,333,803 A | 6/1982 | Seger | |
| 4,750,140 A | 6/1988 | Asano | |
| 4,802,489 A | 2/1989 | Nitzan | |
| 5,551,422 A | 9/1996 | Simonsen | |
| 5,676,143 A | 10/1997 | Simonsen | |
| 5,725,480 A | 3/1998 | Oosta et al. | |
| 5,732,711 A | 3/1998 | Fitzpatrick | |
| 5,743,262 A | 4/1998 | Lepper, Jr. et al. | |
| 5,769,784 A | 6/1998 | Barnett | |
| 5,795,305 A | 8/1998 | Cho et al. | |
| 5,924,996 A | 7/1999 | Cho et al. | |
| 6,226,089 B1 | 5/2001 | Hakamata | |
| 6,240,306 B1 | 5/2001 | Rohrscheib | |
| 6,269,314 B1 | 7/2001 | Iitawaki et al. | |
| 6,280,381 B1 | 8/2001 | Malin et al. | |
| 6,353,226 B1 | 3/2002 | Khalil et al. | |
| 6,615,061 B1 | 9/2003 | Khalil | |
| 2002/0183646 A1 | 12/2002 | Stivoric et al | |
| 2003/0152133 A1 | 8/2003 | Ellenz | |

FOREIGN PATENT DOCUMENTS

| | | |
|---|---|---|
| EP | 0 778 000 A1 | 6/1997 |
| JP | 06-317566 | 11/1994 |
| JP | 7-71945 | 3/1995 |
| JP | 08-322821 | 12/1996 |
| JP | 10-033512 | 2/1998 |

(Continued)

OTHER PUBLICATIONS

Hillson, R.M. et al, "*Facial and Sublingual Temperature Changes Following Intravenous Glucose Injection in Diabetes*," Diabete & Metabolisme, vol. 8, (Paris), pp. 15-19, (1982).

(Continued)

*Primary Examiner*—Eric F. Winakur
(74) *Attorney, Agent, or Firm*—Antonelli, Terry, Stout & Kraus, LLP.

(57) ABSTRACT

Blood sugar levels are measured non-invasively based on temperature measurement. Non-invasively measured blood sugar level values obtained by a temperature measurement scheme are corrected by blood oxygen saturation and blood flow volume, thereby stabilizing the measurement data.

15 Claims, 16 Drawing Sheets

FOREIGN PATENT DOCUMENTS

| | | |
|---|---|---|
| JP | 10-108857 | 4/1998 |
| JP | 11-505451 | 5/1999 |
| JP | 11-155840 | 6/1999 |
| JP | 11-230901 | 8/1999 |
| JP | 11-318872 | 11/1999 |
| JP | 2000-074829 | 3/2000 |
| JP | 2000-506048 | 5/2000 |
| JP | 2000-258343 | 9/2000 |
| JP | 2002-535023 | 10/2002 |
| JP | 2003-510556 | 3/2003 |
| JP | 2003-144421 | 5/2003 |
| WO | 01/28417 | 4/2001 |
| WO | WO 01/28414 | 4/2001 |
| WO | 03/010510 | 2/2003 |

OTHER PUBLICATIONS

Scott, A.R. et al, "*Diabetes Mellitus and Thermoregulation*," Can. J. Physiol. Pharmacol., vol. 65, pp. 1365-1376 (1987).

Journal of the Medical Association of Thailand, vol. 69, No. 3, 1986, pp. 153-157 (Abstract).

BLOOD SUGAR LEVEL MEASURING APPARATUS

BACKGROUND OF THE INVENTION

1. Field of the Invention

The present invention relates to a non-invasive blood sugar level measuring method and apparatus for measuring glucose concentration in a living body without blood sampling.

2. Background Art

Hilson et al. report facial and sublingual temperature changes in diabetics following intravenous glucose injection (Non-Patent Document 1). Scott et al. discuss the issue of diabetics and thermoregulation (Non-Patent Document 2). Based on such researches, Cho et al. suggests a method and apparatus for determining blood glucose concentration by temperature measurement without requiring the collection of a blood sample (Patent Documents 1 and 2).

Various other attempts have been made to determine glucose concentration without blood sampling. For example, a method has been suggested (Patent Document 3) whereby a measurement site is irradiated with near-infrared light of three wavelengths, and the intensity of transmitted light as well as the temperature of the living body is detected. Then, a representative value of the second-order differentiated value of absorbance is calculated, and the representative value is corrected in accordance with the difference between the living body temperature and a predetermined reference temperature. A blood sugar level corresponding to the thus corrected representative value is then determined. An apparatus is also provided (Patent Document 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (Patent Document 5) whereby an output ratio between reference light and the light transmitted by an irradiated sample is taken, and then a glucose concentration is calculated using a linear expression of the logarithm of the output ratio and the living body temperature.

[Non-Patent Document 1] R. M. Hilson and T. D. R. Hockaday, "Facial and sublingual temperature changes following intravenous glucose injection in diabetics," Diabete & Metabolisme, 8, pp. 15–19: 1982

[Non-Patent Document 2] A. R. Scott, T. Bennett, I. A. MacDonald, "Diabetes mellitus and thermoregulation," Can. J. Physiol. Pharmacol., 65, pp. 1365–1376: 1987

[Patent Document 1] U.S. Pat. No. 5,924,996

[Patent Document 2] U.S. Pat. No. 5,795,305

[Patent Document 3] JP Patent Publication (Kokai) No. 2000-258343 A

[Patent Document 4] JP Patent Publication (Kokai) No. 10-33512 A (1998)

[Patent Document 5] JP Patent Publication (Kokai) No. 10-108857 A (1998)

SUMMARY OF THE INVENTION

Glucose (blood sugar) in blood is used for glucose oxidation reaction in cells to produce necessary energy for the maintenance of a living body. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also varies due to factors other than blood glucose concentration. While methods have been proposed to determine blood glucose concentration by temperature measurement without blood sampling, they lack sufficient accuracy.

It is the object of the invention to provide a method and apparatus for determining blood glucose concentration with high accuracy based on temperature data of a subject without blood sampling.

Blood sugar is delivered to the cells throughout the human body via the blood vessel system, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The amount of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. On the assumption that the body temperature is determined by the balance between the amount of energy produced in the body by glucose burning, namely heat production, and heat dissipation such as mentioned above, we set up the following model:

(1) The amount of heat production and the amount of heat dissipation are considered equal.
(2) The amount of heat production is a function of the blood glucose concentration and the amount of oxygen supply.
(3) The amount of oxygen supply is determined by the blood hemoglobin concentration, the blood hemoglobin oxygen saturation, and the volume of blood flow in the capillary blood vessels.
(4) The amount of heat dissipation is mainly determined by heat convection and heat radiation.

The inventors have achieved the present invention after realizing that blood sugar levels can be accurately determined on the basis of the results of measuring the temperature of the body surface and parameters relating to oxygen concentration in blood and blood flow volume, in accordance with the aforementioned model. The parameters can be measured from a part of the human body, such as the fingertip. Parameters relating to convection and radiation can be determined by carrying out thermal measurements on the fingertip. Parameters relating to blood hemoglobin concentration and blood hemoglobin oxygen saturation can be obtained by spectroscopically measuring blood hemoglobin and determining the ratio of hemoglobin bound with oxygen to hemoglobin not bound with oxygen. With regard to the parameters relating to blood hemoglobin concentration and blood hemoglobin oxygen saturation, measurement accuracy would not be significantly lowered if pre-stored constants are employed rather than taking measurements. The parameter relating to the volume of blood flow can be determined by measuring the amount of heat transfer from the skin.

In one aspect, the invention provides a blood sugar level measuring apparatus comprising:

a heat amount measurement portion for measuring a plurality of temperatures derived from a body surface and obtaining information used for calculating the amount of heat transferred by convection and the amount of heat transferred by radiation, both related to the dissipation of heat from said body surface;

an oxygen amount measuring portion for obtaining information about blood oxygen amount;

a storage portion for storing a relationship between parameters corresponding to said plurality of temperatures and blood oxygen amount and blood sugar levels;

a calculating portion which converts a plurality of measurement values fed from said heat amount measuring portion and said oxygen amount measurement portion into said parameters, and which computes a blood sugar level by applying said parameters to said relationship stored in said storage portion;

a display portion for displaying the blood sugar level calculated by said calculating portion; and a warm-up control portion for conducting a warm-up, wherein said oxygen amount measuring portion comprises a blood flow volume measuring portion for obtaining information about blood flow volume and an optical measuring portion for obtaining the hemoglobin concentration and hemoglobin oxygen saturation in blood, wherein the blood flow volume measuring portion comprises a body-surface contact portion, a first temperature detector disposed adjacent to the body-surface contact portion, a second temperature detector for detecting the temperature at a position spaced apart from the body-surface contact portion, and a heat conducting member connecting the body-surface contact portion and the second temperature detector, and wherein the warm-up control portion determines whether or not the temperature measured by the heat amount measuring portion or the blood flow volume measuring portion during warm-up is within a predetermined temperature range.

In another aspect, the invention provides a blood sugar level measuring apparatus comprising:

an ambient temperature measuring device for measuring ambient temperature;

a body-surface contact portion to which a body surface is brought into contact;

an adjacent-temperature detector disposed adjacent to said body-surface contact portion;

a radiant heat detector for measuring radiant heat from said body surface;

a heat conducting member disposed in contact with said body-surface contact portion;

an indirect-temperature detector disposed at a position that is adjacent to said heat conducting member and that is spaced apart from said body-surface contact portion, said indirect-temperature detector measuring temperature at the position spaced apart from said body-surface contact portion;

a light source for irradiating said body-surface contact portion with light of at least two different wavelengths;

a photodetector;

a converter for converting outputs from said adjacent-temperature detector, said indirect-temperature detector, said ambient temperature detector, said radiant heat detector and said photodetector, into individual parameters;

a calculating portion in which a relationship between said parameters and blood sugar levels is stored in advance, and which calculates a blood sugar level by applying said parameters to said relationship;

a display for displaying the result outputted from said calculating portion; and a warm-up control portion for conducting a warm-up, wherein the warm-up control portion determines whether or not the temperature measured by the ambient temperature measuring device, the adjacent-temperature detector, or the indirect-temperature detector during warm-up is within a predetermined temperature range.

In yet another aspect, the invention provides a blood sugar level measuring apparatus comprising:

an ambient temperature measuring device for measuring ambient temperature;

a body-surface contact portion to which a body surface is brought into contact;

an adjacent-temperature detector disposed adjacent to said body-surface contact portion;

a radiant heat detector for measuring radiant heat from said body surface;

a heat conducting member disposed in contact with said body-surface contact portion;

an indirect-temperature detector disposed at a position that is adjacent to said heat conducting member and that is spaced apart from said body-surface contact portion, said indirect-temperature detector measuring temperature at the position spaced apart from said body-surface contact portion;

a storage portion where information about blood hemoglobin concentration and blood hemoglobin oxygen saturation is stored;

a converter for converting outputs from said adjacent-temperature detector, said indirect-temperature detector, said ambient temperature measuring device and said radiant heat detector, into a plurality of parameters;

a calculating portion in which a relationship between said parameters and blood sugar levels is stored in advance, said calculating portion including a processing portion for calculating a blood sugar level by applying said parameters to said relationship;

a display for displaying the blood sugar level outputted from said calculating portion; and a warm-up control portion for conducting a warm-up, wherein the warm-up control portion determines whether or not the temperature measured by the ambient temperature measuring device, the adjacent-temperature detector, or the indirect-temperature detector during warm-up is within a predetermined temperature range.

In accordance with the invention, a blood sugar level measuring apparatus can be provided that is capable of determining blood sugar level in a non-invasive manner and yet with the same level of accuracy as that achieved by the conventional invasive method.

DESCRIPTION OF THE PREFERRED EMBODIMENTS

The invention will now be described by way of preferred embodiments thereof with reference made to the drawings.

Initially, the above-mentioned model will be described in more specific terms. Regarding the amount of heat dissipation, convective heat transfer, which is one of the main causes of heat dissipation, is related to temperature difference between the ambient (room) temperature and the body-surface temperature. The amount of heat dissipation due to radiation, another main cause of dissipation, is proportional to the fourth power of the body-surface temperature according to the Stefan-Boltzmann law. Thus, it can be seen that the amount of heat dissipation from the human body is related to the room temperature and the body-surface temperature. Another major factor related to the amount of heat production, the oxygen supply amount, is expressed as the product of hemoglobin concentration, hemoglobin oxygen saturation, and blood flow volume.

The hemoglobin concentration can be measured based on the absorbance of light at the wavelength (iso-absorption wavelength) at which the molar absorption coefficient of the oxy-hemoglobin and that of the reduced (deoxygenated) hemoglobin are equal. The hemoglobin oxygen saturation can be measured by measuring the absorbance of the iso-absorption wavelength and at least one other wavelength at which the ratio of the molar absorption coefficient of the oxy-hemoglobin to that of the reduced (deoxygenated) hemoglobin is known, and then solving simultaneous equations. Thus, the hemoglobin concentration and the hemoglobin oxygen saturation can be obtained by measuring absorbance at at least two wavelengths.

The rest is the blood flow volume, which can be measured by various methods. One example will be described below.

Figure 1:
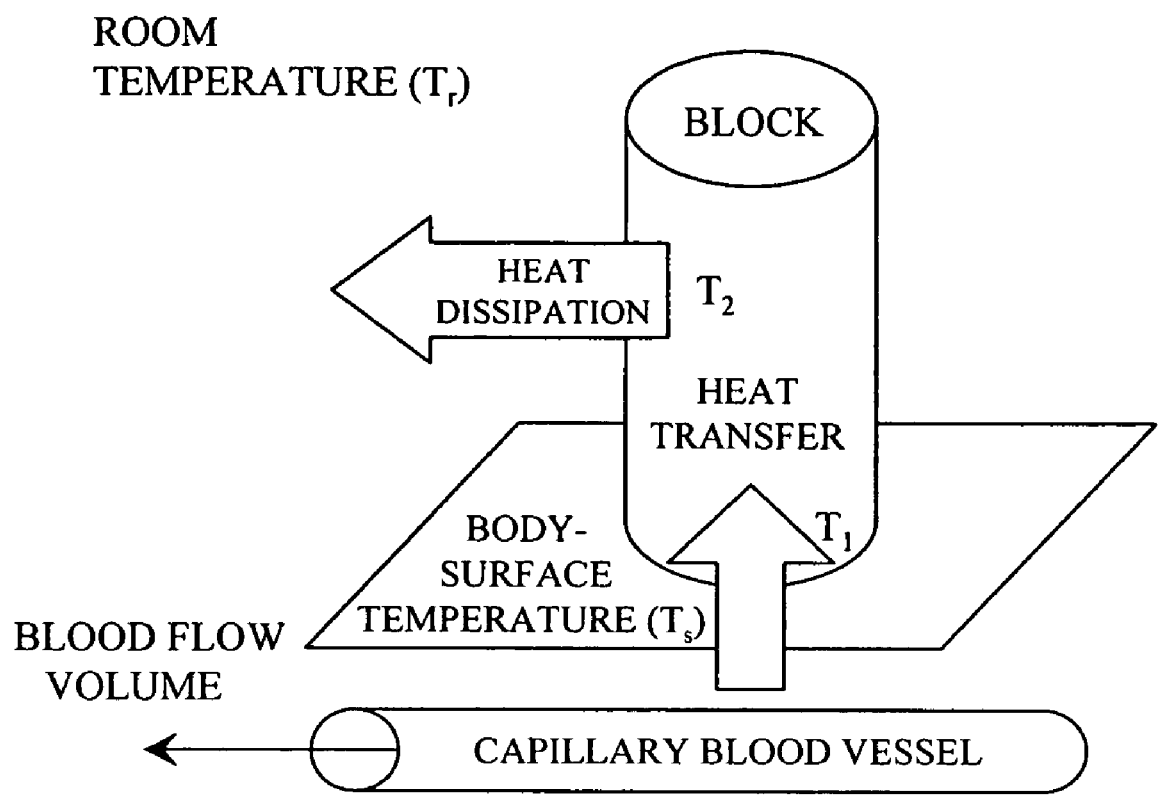
FIG. 1 shows a model of the transfer of heat from a body surface to a block.

FIG. 1 shows a model for the description of the transfer of heat from the body surface to a solid block with a certain heat capacity as the block is brought into contact with the body surface for a certain time and then separated. The block is made of resin such as plastic or vinyl chloride. In the illustrated example, attention will be focused on the chronological variation of a temperature $T_1$ of a portion of the block in contact with the body surface, and the chronological variation of a temperature $T_2$ at a point on the block away from the body surface. The blood flow volume can be estimated by monitoring mainly the chronological variation of the temperature $T_2$ (at the spatially distant point on the block). The details will be described later.

Before the block comes into contact with the body surface, the temperatures $T_1$ and $T_2$ at the two points of the block are equal to the room temperature $T_r$. When a body-surface temperature $T_s$ is higher than the room temperature $T_r$, the temperature $T_1$ swiftly rises as the block comes into contact with the body surface, due to the transfer of heat from the skin, and it approaches the body-surface temperature $T_s$. On the other hand, the temperature $T_2$, which is lower than the temperature $T_1$ due to the dissipation of the heat conducted through the block from its surface, rises more gradually than the temperature $T_1$. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the coefficient of heat transfer from the capillary blood vessels to the surrounding cell tissues is given as a function of the blood flow volume. Thus, by measuring the amount of heat transfer from the body surface to the block by monitoring the chronological variation of the temperatures $T_1$ and $T_2$, the amount of heat transmitted from the capillary blood vessels to the cell tissues can be estimated, which in turn makes it possible to estimate the blood flow volume.

Figure 2:
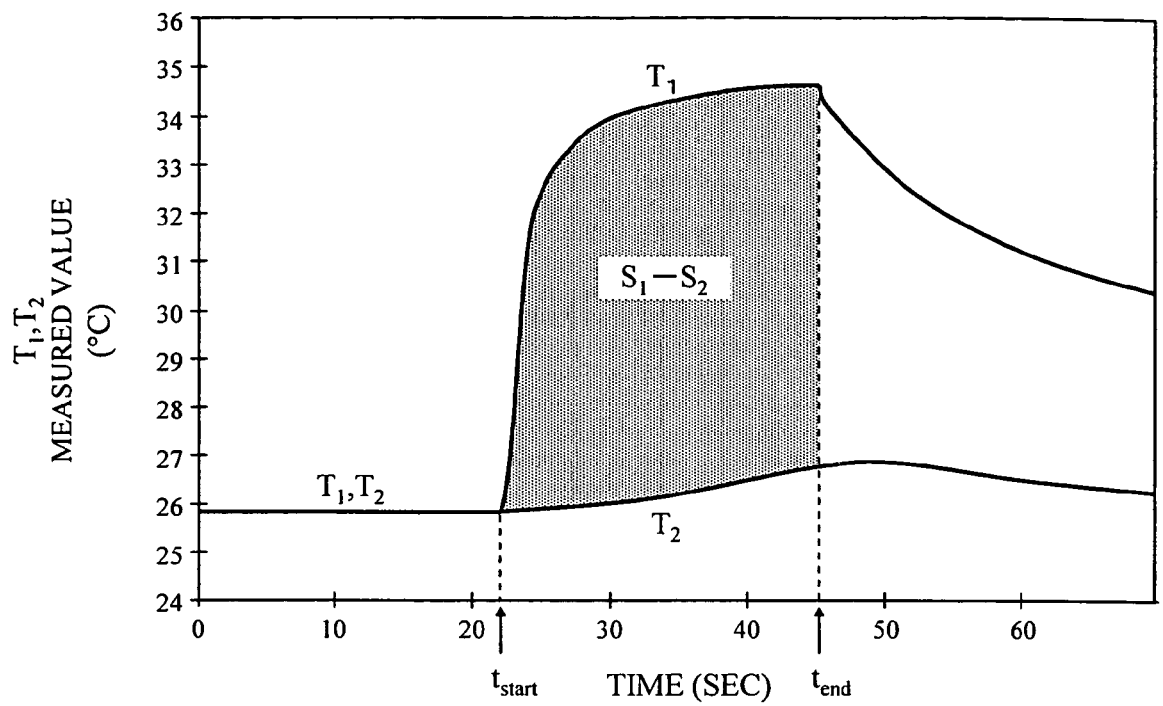
FIG. 2 shows changes in measurement values of temperatures $T_1$ and $T_2$ with time.

FIG. 2 shows the chronological variation of the measured values of the temperature $T_1$ at the portion of the block in contact with the body surface and the temperature $T_2$ at the point on the block away from the body-surface contact position. As the block comes into contact with the body surface, $T_1$ swiftly rises, and it gradually drops as the block is brought out of contact.

Figure 3:
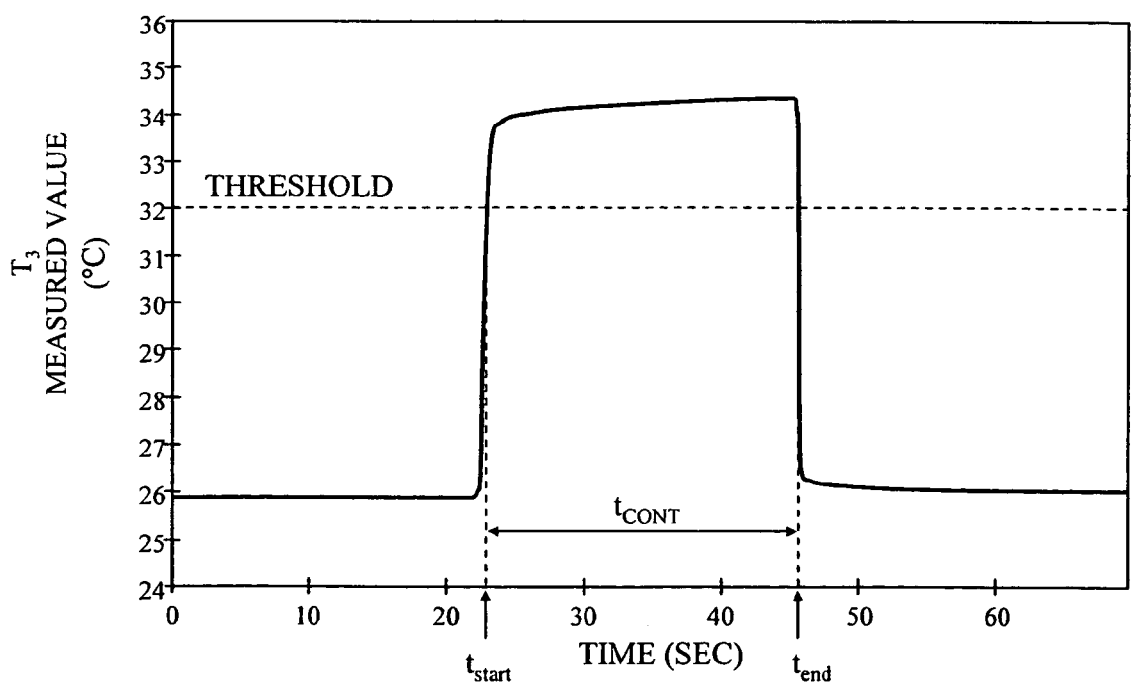
FIG. 3 shows an example of the measurement of a change in temperature $T_3$ with time.

FIG. 3 shows the chronological variation of the measured value of a temperature $T_3$ measured by a radiation temperature detector. As the temperature $T_3$ measured is that due to the radiation from the body surface, this sensor can more sensitively react to temperature changes than other sensors. Because radiation heat propagates as an electromagnetic wave, it can transmit temperature changes instantaneously. Thus, as shown in FIG. 15, reference to which will be made below, by providing the radiation temperature detector near the position where the block is in contact with the body surface in order to detect the radiant heat from the body surface, contact start time $t_{start}$ and contact end time $t_{end}$ of contact between the block and body surface can be detected based on a change in temperature $T_3$. For example, when a temperature threshold value is set as shown in FIG. 3, it can be determined that contact start time $t_{start}$ is when the temperature threshold value is exceeded, and contact end time $t_{end}$ is when the measured temperature drops below the temperature threshold value. The temperature threshold value may be set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining factors a, b, c, and d by the non-linear least-squares method.

For the resultant approximate expression, T is integrated between time $t_{start}$ and time $t_{end}$ to obtain a value $S_1$.

Similarly, an integrated value $S_2$ is calculated from the $T_2$ measured value. The smaller the $(S_1-S_2)$ is, the larger the amount of transfer of heat from the finger surface to the position of $T_2$. $(S_1-S_2)$ becomes larger with increasing finger contact time $t_{CONT}(=t_{end}-t_{start})$. Thus, $a_5/(t_{CONT}\times(S_1-S_2))$ is designated as a parameter $X_5$ indicating the volume of blood flow, where $a_5$ is a proportionality coefficient.

It will be seen from the above description that the measured quantities necessary for the determination of blood glucose concentration by the aforementioned model are the room temperature (ambient temperature), body surface temperature, temperature changes in the block in contact with the body surface, the temperature due to radiation from the body surface, and the absorbance of at least two wavelengths.

Figure 4:
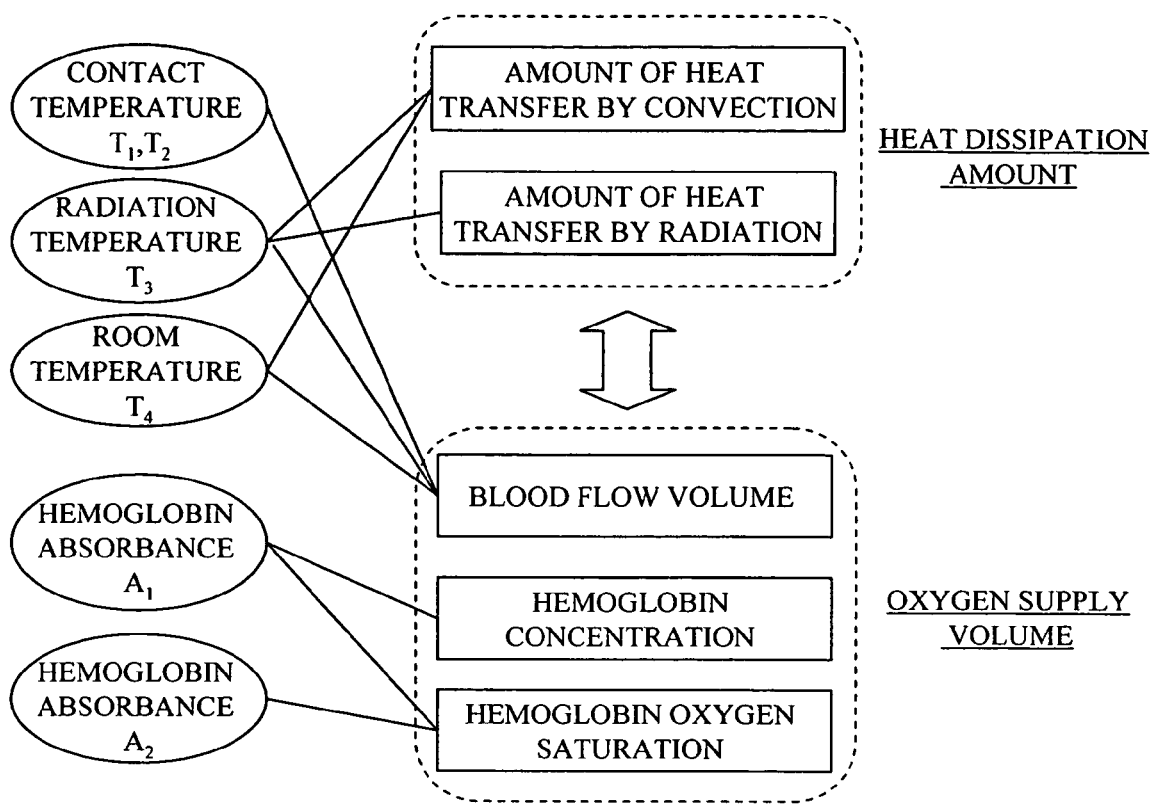
FIG. 4 shows the relationship between measurement values obtained by various sensors and parameters derived therefrom.

FIG. 4 shows the relationships between the measured values provided by various sensors and the parameters derived therefrom. A block is brought into contact with the body surface, and chronological changes in the two kinds of temperatures $T_1$ and $T_2$ are measured by two temperature sensors provided at two locations of the block. Separately, the radiation temperature $T_3$ on the body surface and the room temperature $T_4$ are measured. Absorbance $A_1$ and $A_2$ are measured at at least two wavelengths related to the absorption of hemoglobin. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. Absorbance $A_1$ provides a parameter relating to hemoglobin concentration. Absorbance $A_1$ and $A_2$ provide parameters relating to hemoglobin oxygen saturation.

Hereafter, an example of the apparatus for non-invasively measuring blood sugar levels according to the principle of the invention will be described.

Figure 5:
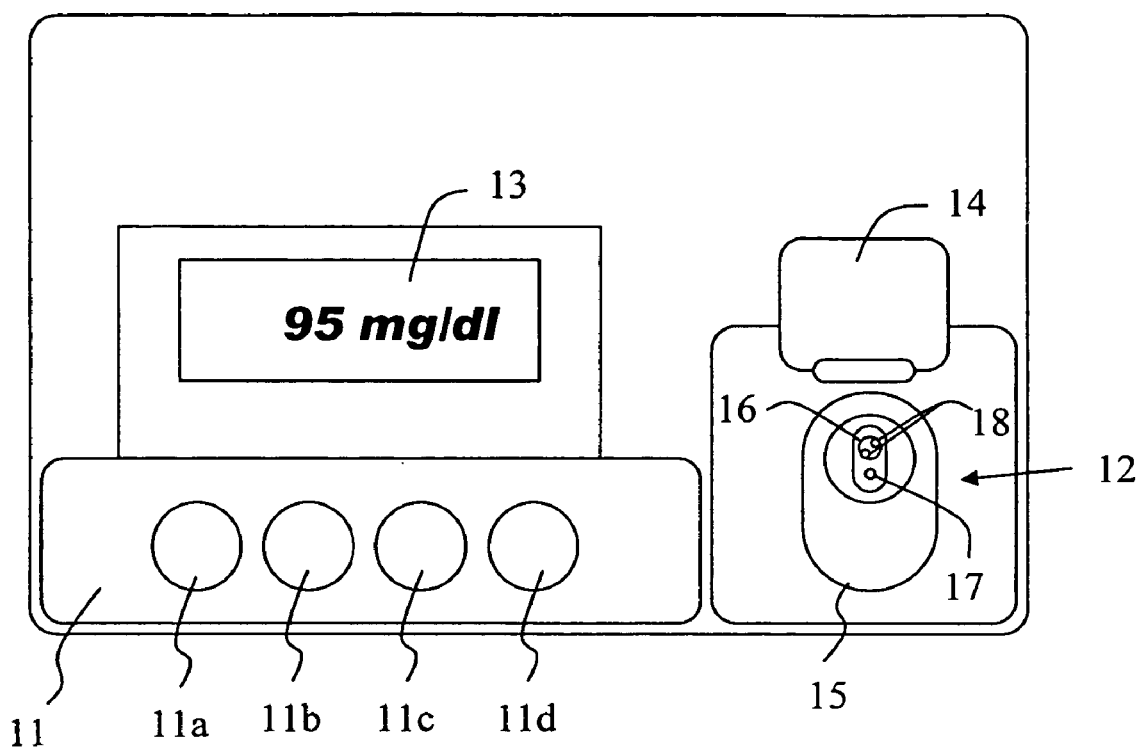
FIG. 5 shows a top plan view of a blood sugar level measuring apparatus according to the present invention.

FIG. 5 shows a top plan view of the non-invasive blood sugar level measuring apparatus according to the invention. While in this example the skin on the ball of the fingertip is used as the body surface, other parts of the body surface may be used.

On the upper surface of the apparatus are provided an operating portion 11, a measurement portion 12 where the finger to be measured is to be placed, and a display portion 13 for displaying the result of measurement, the state of the apparatus, measured values, and so on. The operating portion 11 includes four push buttons 11a to 11d for operating the apparatus. The measurement portion 12 has a cover 14 which, when opened (as shown), reveals a finger rest portion 15 with an oval periphery. The finger rest portion 15 accommodates an open end 16 of a radiation temperature sensor portion, a contact temperature sensor portion 17, and an optical sensor portion 18.

Figure 6:
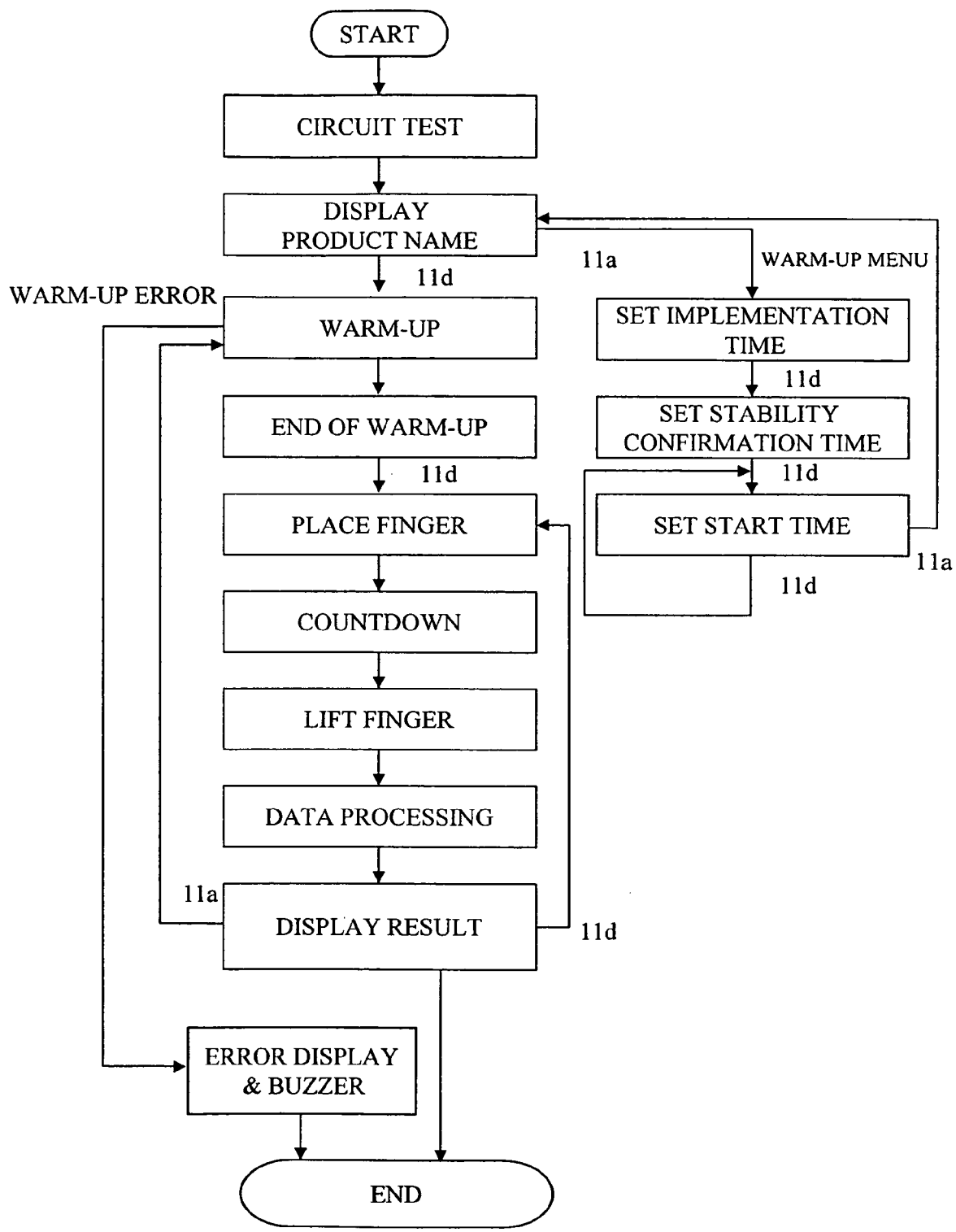
FIG. 6 shows the operating procedure for the apparatus.
Figure 7:
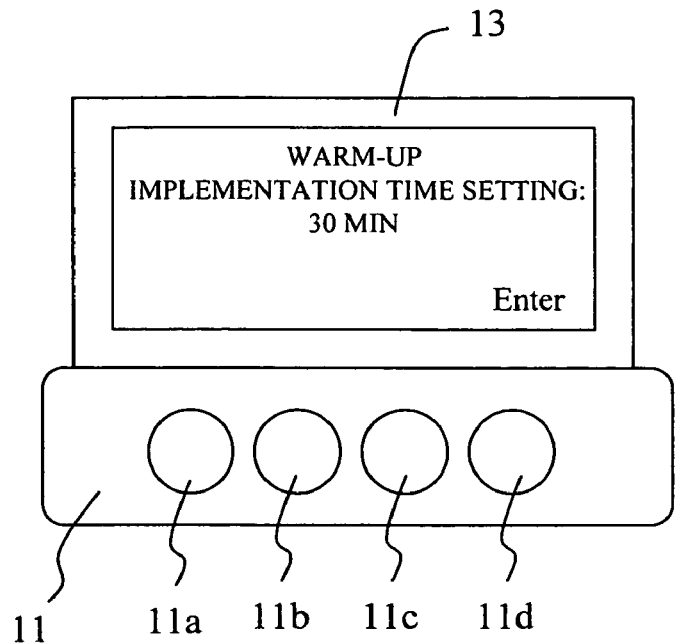
FIG. 7 shows an example of the setting of the time of implementation of a warm-up.
Figure 8:
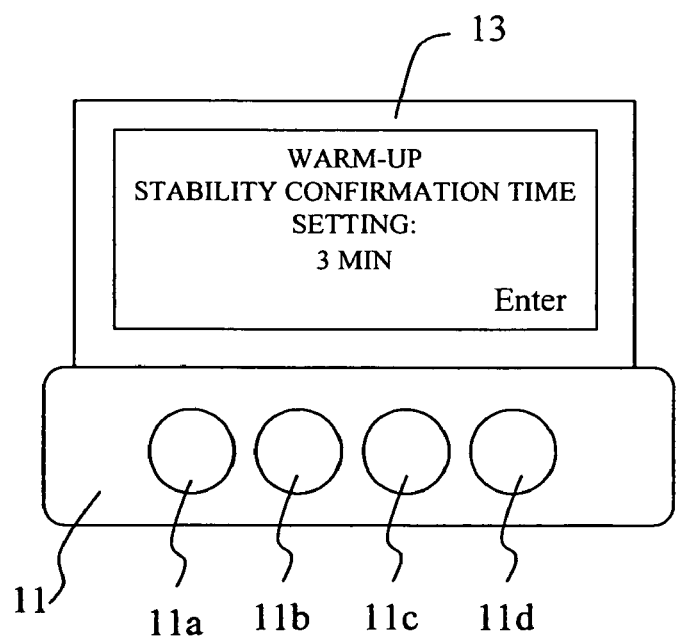
FIG. 8 shows an example of the setting of a stability confirmation time for a warm-up.
Figure 9:
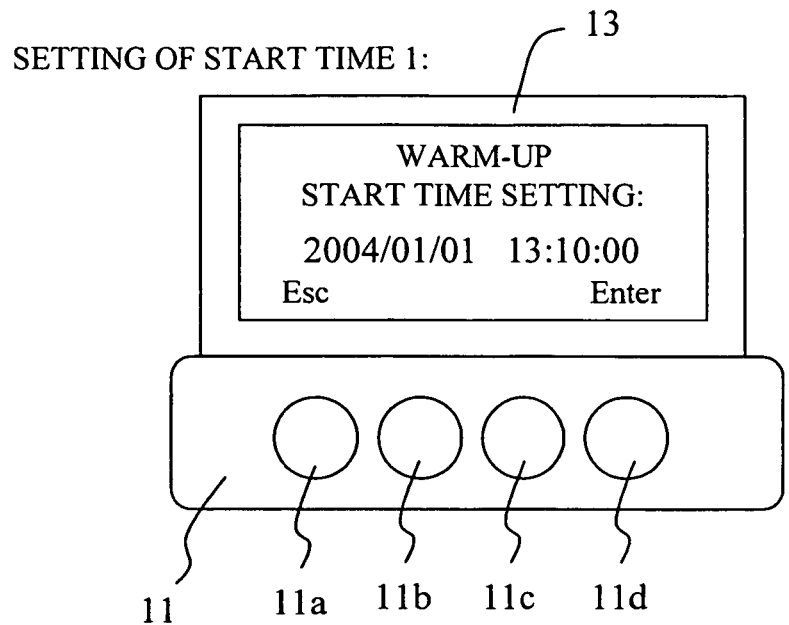
FIG. 9 shows an example of the setting of a warm-up start time 1.
Figure 10:
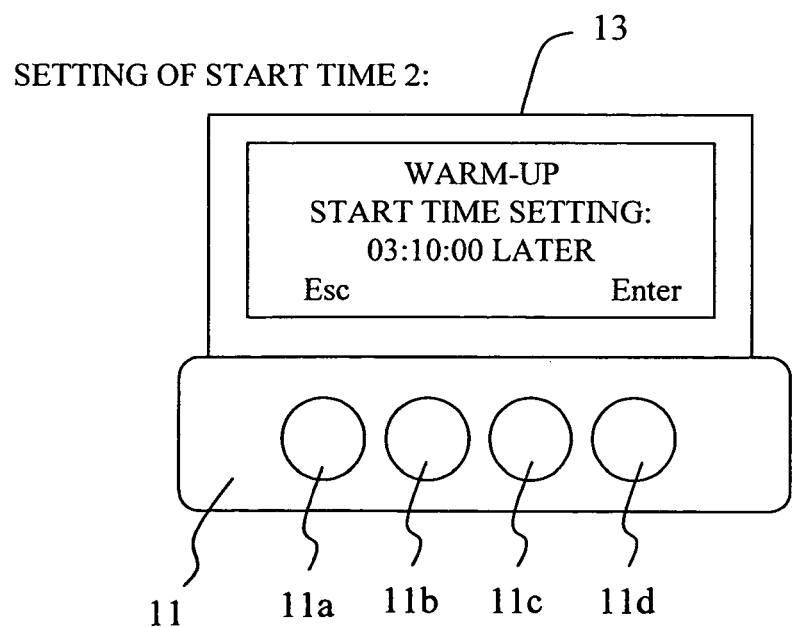
FIG. 10 shows an example of the setting of a warm-up start time 2.

FIG. 6 shows the operation procedure for the apparatus. As a button in the operating portion is pressed and the apparatus is turned on, a checking program is activated, whereby the electronic circuitry is automatically checked. Then, the product name is displayed on the LCD, when the apparatus enters into a key-input waiting mode. First, prior to measurement, the button 11a is pressed to thereby activate a warm-up menu, and then a warm-up implementation time, a stability confirmation time, and a start time are set in the mentioned order. FIG. 7 shows a setting of the warm-up implementation time. In this setting, a maximum time is set for the warm-up. After the warm-up implementation time is thus set, the button 11d is pressed. Then, the warm-up stability confirmation time is set, as shown in FIG. 8. In order to make sure that the room temperature is stable, temperatures at two locations spaced apart from one another by a certain distance are measured, and it is checked to see if the temperatures are the same. The "stability confirmation time" refers to this certain time duration. When the two temperatures are compared, numbers after the decimal point are not used. After the stability confirmation time is set, the button 11d is pressed. Then, the warm-up start time is set. As shown in FIGS. 9 and 10, there are two modes for designating the start time, namely start time 1 and start time 2, of which either one or the other is set. In start time 1, the date and time when the warm-up is to end are set. In start time 2, the duration of time that is to elapse before the warm-up is to end is set. After the start time is thus set, by pressing the button 11d repeatedly, the start time for the next warm-up can be set. A plurality of warm-up start times can be set. After the warm-up start time has thus been set, the button 11d is pressed, whereby the settings of a warm-up are completed, and the LCD returns to the display of the product name.

Figure 11:
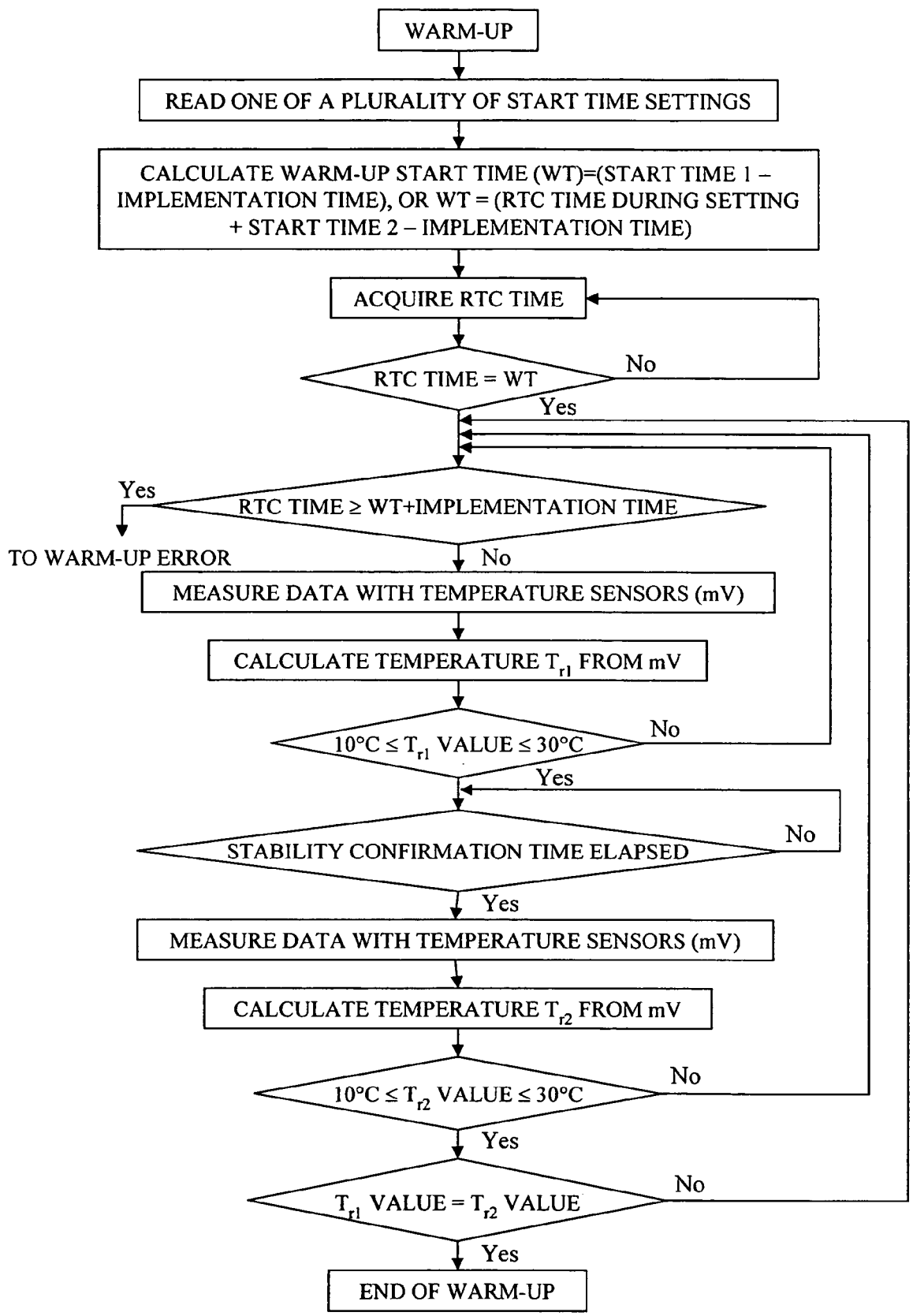
FIG. 11 shows a warm-up check procedure.

By pressing the button 11d while the product name is being displayed, a warm-up checking procedure is activated, as shown in FIG. 11. In this procedure, one of a plurality of start times that have been set is read, and a warm-up start time (WT) is calculated. In the case where the warm-up start time is set in start time 1, WT=start time 1−implementation time. In the case where the start time is set in start time 2, WT=(real-time clock (RTC) time upon setting in the warm-up menu+start time 2−implementation time). Thereafter, the RTC time is acquired, and the acquisition of the RTC time and comparison are repeated until the current RTC time is equal to the value of WT. When RTC time=WT, the following procedure is carried out for checking the warm-up.

Figure 12:
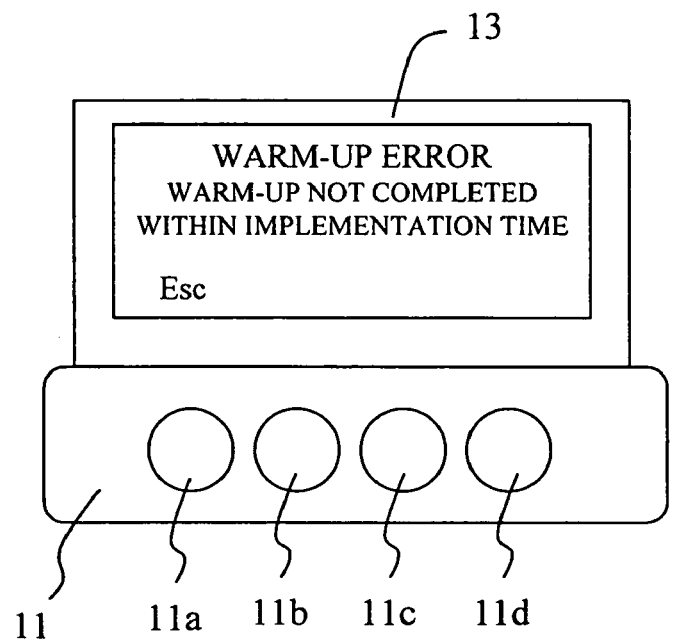
FIG. 12 shows an example of a screen indicating a warm-up error.
Figure 13:
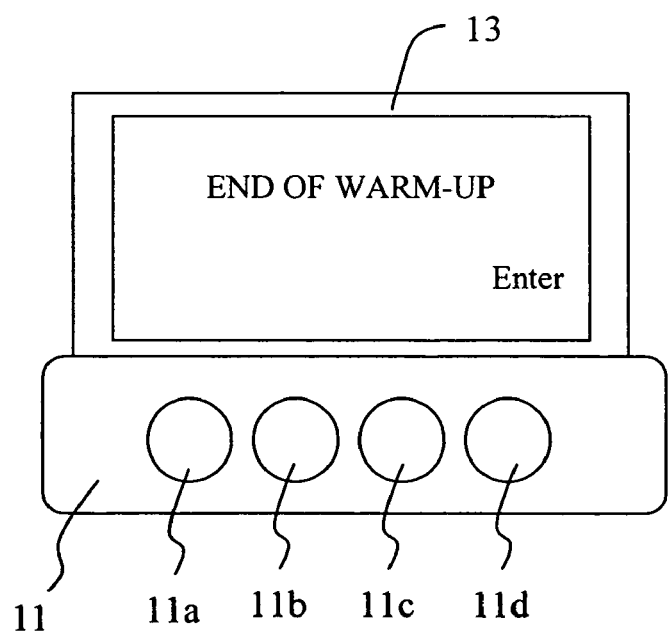
FIG. 13 shows an example of the screen indicating the end of a warm-up.

(Warm-up Checking Procedure)
(1) The RTC time is compared with the time (WT+implementation time). If RTC time≧(WT+implementation time), this indicates that the warm-up did not normally end within the implementation time, and a warm-up error is indicated as shown in FIG. 12.
(2) If RTC time<(WT+implementation time), data is measured using the temperature sensors.
(3) Temperature T ($T_{r1}$) is calculated from the data, using the following temperature conversion formula:

$$T=a_0 X^{b1}+a_1 X^{b2}+a_2 X^{b3}+a_3 X^{b4}$$

where
T: temperature
X: temperature sensor data
$a_0, a_1, a_2, a_3$: coefficients for temperature sensors
b1, b2, b3, b4: exponential coefficients for temperature sensors
(4) The range of temperature $T_{r1}$ is checked. If 10° C.≦$T_{r1}$ value≦30° C., the following step (5) is taken. Otherwise, the checking procedure is repeated from (1).
(5) Wait until the stability confirmation time elapses.
(6) Data is measured again using the temperature sensors.
(7) Temperature T ($T_{r2}$) is calculated from the data, using the said temperature conversion formula.
(8) The range of temperature $T_{r2}$ is checked. If 10° C.≦$T_{r2}$ value≦30° C., the following step (9) is taken. Otherwise, the checking procedure is repeated from (1).
(9) It is determined whether the temperature $T_{r1}$ value is equal to the temperature $T_{r2}$ value. If $T_{r1}$ value=$T_{r2}$ value (note that errors of the order of ±0.5° are tolerated), the warm-up checking procedure has been normally completed, and the end of warm-up is indicated on the LCD, as shown in FIG. 13. If the $T_{r1}$ and $T_{r2}$ values are not equal, the checking procedure is repeated from (1). The comparison of the $T_{r1}$ and $T_{r2}$ values is carried out using rounded values and no data after the decimal point needs to be used.

If temperature $T_{r1}$ is measured only once, it is sometimes difficult to conclude that the apparatus is in a stable-temperature environment even if the value of temperature $T_{r1}$ is in the range between 10° C. and 30° C., for there is the possibility that temperature $T_{r1}$ is increasing or decreasing. Thus, by measuring the temperature twice, i.e., by measuring temperatures $T_{r1}$ and $T_{r2}$ and then comparing them, it becomes possible to determine whether the apparatus is in a more stable temperature environment. It could be possible to determine that the apparatus is in a stable temperature environment based on a single measurement of temperature $T_{r1}$ in cases where the apparatus has been acclimatized to the temperature of the measuring environment for a long time prior to measurement. However, whether or not the ambient temperature is stable can be more accurately determined by measuring the temperature twice or more times and comparing the measured temperatures. When the temperature is measured twice or more times, the interval of temperature measurements should be somewhere between 30 seconds and 10 minutes.

If the temperature of the environment in which measurement is to take place is low (lower than 10° C.), the blood flow inside the body is curbed, the amount of heat generated from inside the body decreases, and the body-surface temperature also decreases. As a result, accurate measurement of the generated-heat amount and the body-surface temperature is prevented and it becomes difficult to calculate an accurate blood sugar level. On the other hand, if the temperature of the measurement environment is high (more than 30° C.), the body temperature is reduced by perspiration. As a result, the amount of heat generated from inside the body and the body-surface temperature cannot be accurately measured, and it becomes difficult to calculate an accurate blood sugar level. Thus, by conducting the measurement in environments with temperatures in the range between 10° C. and 30° C., the amount of heat generated from inside the body and the body-surface temperature can be measured reasonably stably, which makes it possible to calculate an accurate blood sugar level.

An example of the calculation using the temperature conversion formula is shown below. When the values of the coefficients $a_0$ to $a_3$ for the temperature sensors, the exponential coefficients $b_1$ to $b_4$ for the temperature sensors, and data X from the temperature sensors are as follows, T=26.18° C.

$a_0 = -32.981899992$ $a_1 = 7.2681099983 \times 10^{-6}$ $a_2 = -1.1607029998 \times 10^{-20}$ $a_3 = 6.6745269979 \times 10^{-35}$ $b_1 = 0$ $b_2 = 1$ $b_3 = 3$ $b_4 = 5$

X=8737573

The user can be informed of the fact that he or she can now take measurements by displaying a message "WARM-UP COMPLETED." As the button 11d is pressed while this message is on the display, a message "PLACE FINGER" is displayed on the LCD. As the user places his or her finger on the finger rest portion, a countdown is displayed on the LCD. When the countdown is over, the LCD displays "LIFT FINGER." As the user lifts his or her finger from the finger rest portion, the LCD displays "DATA PROCESSING." Thereafter, a blood sugar level is displayed on the LCD, and the blood sugar level is stored in an IC card, together with the date and time. The user reads the blood sugar level that is being displayed and then presses the button 11d in the operating portion. This causes the message "PLACE FINGER" to appear on the LCD approximately one minute later, indicating that the apparatus is ready for the next measurement. As the button 11a is pressed with the result display screen showing the blood sugar level, the above-described warm-up checking procedure is activated. Thus, the warm-up checking procedure can be carried out at a plurality of start times that are set. By conducting the warm-up checking procedure, the temperature of the apparatus can be stabilized in the measuring environment, and stable data can be obtained over a plurality of measurements, which makes it possible to calculate blood sugar level more accurately.

Figure 14:
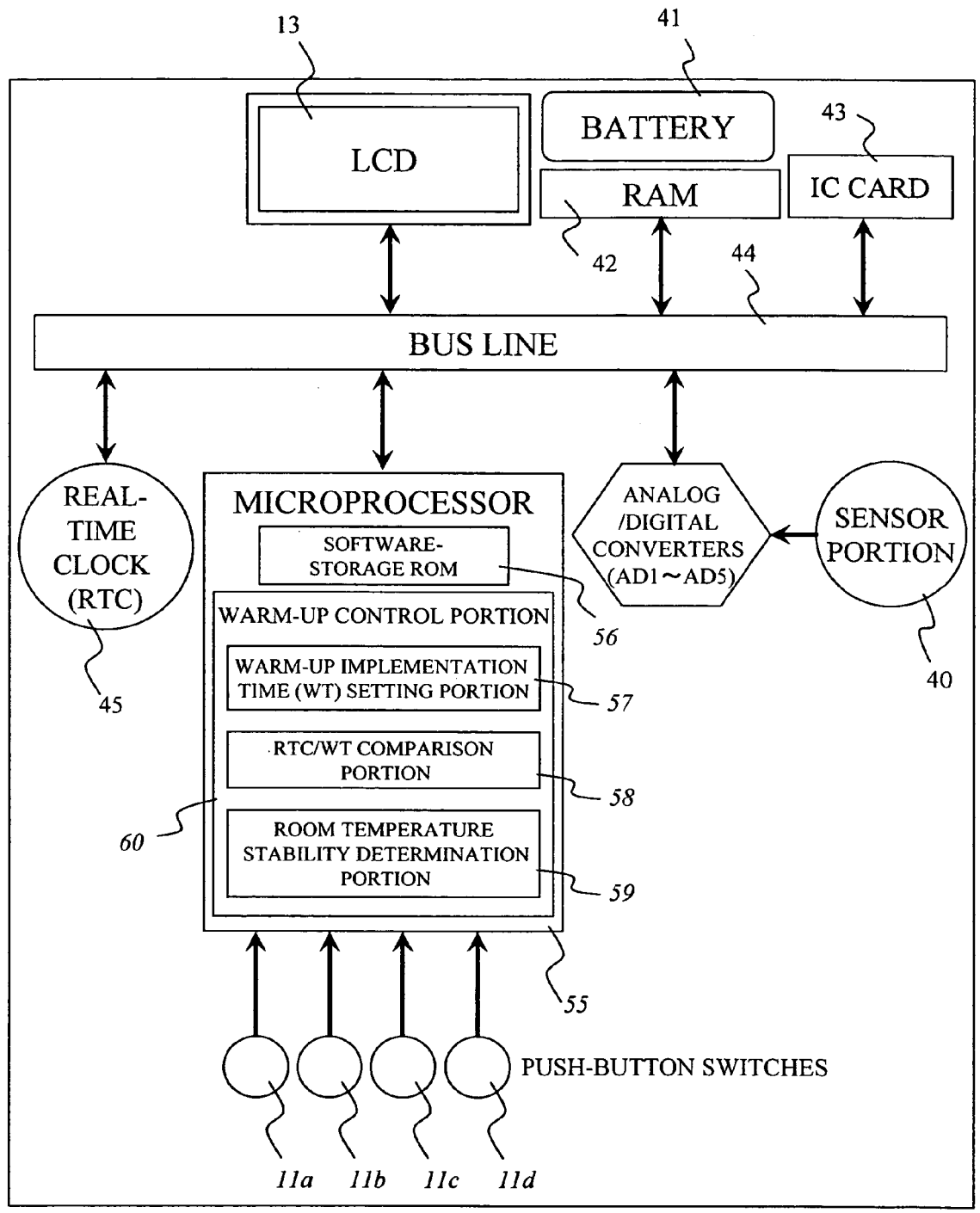
FIG. 14 shows a functional block diagram of the apparatus.

FIG. 14 shows a functional block diagram of the apparatus. The apparatus operates on a battery 41. Signals measured by a sensor portion 40 including temperature and optical sensors are fed to analog/digital converters AD1 to AD5 provided for the individual signals and are converted into digital signals therein. A microprocessor 55 includes a ROM 56 for storing software, a warm-up implementation time (WT) setting portion 57, a real-time clock (RTC)/WT comparison portion 58, and a room-temperature stability determination portion 59. The warm-up implementation time (WT) setting portion 57, the real-time clock (RTC)/WT comparison portion 58, and the room-temperature stability determination portion 59 together form a warm-up control portion 60. In the warm-up implementation time (WT) setting portion 57, the warm-up implementation time, stability confirmation time, and start time are set. In the real-time clock (RTC)/WT comparison portion 58, whether or not it is time for starting the warm-up checking procedure is determined based on a comparison with the time according to a real-time clock 45. In the room temperature stability determination portion 59, it is checked to see whether or not the apparatus is in a temperature environment suitable for measurement. Specifically, it is determined whether the room temperature is in the range between 10° C. and 30° C. In the case where the room temperature is measured twice or more times and the measurements are compared with one another, it is determined whether or not the temperature values $T_{r1}$ and $T_{r2}$ are equal. During the comparison of $T_{r1}$ and $T_{r2}$ values, errors of the order of ±0.5 degrees are tolerated. Alternatively, the comparison may be performed using rounded values to disregard the data after the decimal point.

Peripheral circuits of the microprocessor 55 include the analog/digital converters AD1 to AD5, LCD 13, RAM 42, IC card 43, and real-time clock 45. The microprocessor 55 can access these devices via a bus lines 44. The push buttons 11a to 11d are each coupled with the microprocessor 55.

Figure 15A:
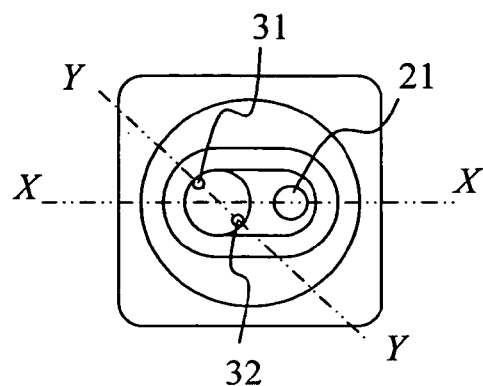
FIG. 15 shows a measuring portion in detail.
Figure 15B:
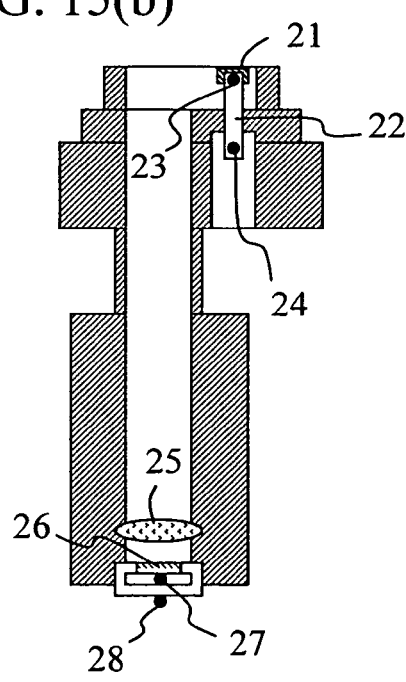

FIG. 15 shows the details of the measurement portion. FIG. 15(a) is a top plan view, FIG. 15 (b) is a cross section taken along line X—X of (a), and FIG. 15 (c) is a cross section taken along Y—Y of FIG. 15 (a).

First, temperature measurement by the non-invasive blood sugar level measuring apparatus according to the invention will be described. A thin plate 21 of a highly heat-conductive material, such as gold, is disposed on a portion where a measured portion (ball of the finger) is to come into contact. A bar-shaped heat-conductive member 22 made of a material with a heat conductivity lower than that of the plate 21, such as polyvinylchloride, is thermally connected to the plate 21 and extends into the apparatus. The temperature sensors include a thermistor 23, which is an adjacent-temperature detector with respect to the measured portion for measuring the temperature of the plate 21. There is also a thermistor 24, which is an indirect-temperature detector with respect to the measured portion for measuring the temperature of a portion of the heat-conducting member away from the plate 21 by a certain distance. An infrared lens 25 is disposed inside the apparatus at such a position that the measured portion (ball of the finger) placed on the finger rest portion 15 can be seen through the lens. Below the infrared lens 25, there is disposed a pyroelectric detector 27 via an infrared radiation-transmitting window 26. Another thermistor 28 is disposed near the pyroelectric detector 27.

Thus, the temperature sensor portion of the measurement portion has four temperature sensors, and they measure four kinds of temperatures as follows:

(1) Temperature on the finger surface (thermistor 23): $T_1$.
(2) Temperature of the heat-conducting member (thermistor 24): $T_2$.
(3) Temperature of radiation from the finger (pyroelectric detector 27): $T_3$.
(4) Room temperature (thermistor 28): $T_4$.

For the measurement of room temperature during the warm-up of the apparatus, three of the aforementioned four temperature sensors can be used. Specifically, they are the thermistor 23 attached to the plate 21, the thermistor 24, which measures the temperature at a portion of the heat-conducting member that is spaced apart from the plate 21 by a predetermined distance, and the thermistor 28 disposed within the apparatus.

In order to achieve a highly accurate measurement, the temperature inside the apparatus must be stable. For example, in the event that the apparatus is brought from a warm room into a cold room quickly, although the thermistor 23 disposed on the surface reacts quickly and provide a reduced temperature reading, the temperature inside the apparatus does not drop to the room temperature immediately. Thus, it takes some time before the temperature of the apparatus is stabilized. There is a slight difference in temperature readings between the sensor inside the apparatus and the sensor on the outside. The thermistor 28 disposed inside the apparatus is not easily influenced by various factors of the measuring environment, such as draft. While the thermistor 24 for measuring the temperature at a portion of the heat-conducting member is influenced by the temperature of the finger that has previously been measured, it is not easily influenced by draft, for example. The thermistor 23 attached to the plate 21 is easily influenced by the temperature of the previously measured finger or draft, for example. These comparisons indicate that the temperature sensor (thermistor 28) that is located the most towards the back of the apparatus and that is the most distant from room temperature among the temperature sensors of the apparatus is the most suitable for the purpose of determining the stability of the apparatus temperature. The thermistor 28 is followed in terms of priority by the thermistor 24 for measuring the temperature at a portion of the heat-conducting member, and by the thermistor 23 attached to the plate 21.

From the viewpoint of determining whether or not the room temperature is in the range between 10° C. and 30° C. as specified by the apparatus, the temperature sensor that is the closest to room temperature among the temperature sensors of the apparatus is the most suitable. In this case, the order of priority of the sensors is as follows: (1) plate-attached thermistor 23, which is capable of measuring room temperature more accurately because it is located the closest to the air of room temperature; (2) thermistor 24 measuring the temperature of a portion of the heat-conducting member, which is located at an intermediate position between the thermistors 23 and 28 as regards the air of room temperature; and (3) thermistor 28 disposed inside the apparatus, which is the most distant from the air of room temperature.

Thus, in the present apparatus, the thermistor 28 disposed inside the apparatus is used for the determination of the stability of the apparatus temperature, and the thermistor 23 attached to the plate 21 is used for the determination of the room temperature of the environment in which the apparatus is used.

Figure 15C:
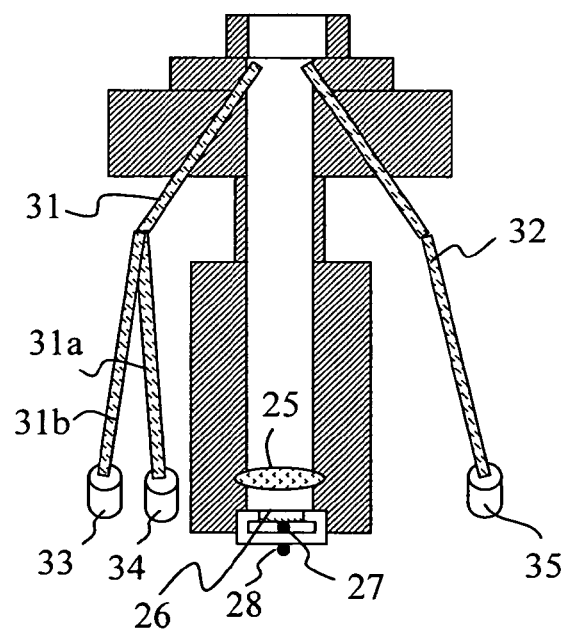

The optical sensor portion 18 will be described. The optical sensor portion measures the hemoglobin concentration and hemoglobin oxygen saturation for obtaining the oxygen supply amount. For measuring the hemoglobin concentration and hemoglobin oxygen saturation, absorbance must be measured at at least two wavelengths. FIG. 15(c) shows an example of an arrangement for performing the two-wavelength measurement using two light sources 33 and 34 and one detector 35.

Inside the optical sensor portion 18, there are disposed the end portions of two optical fibers 31 and 32. The optical fiber 31 is for irradiating light, and the optical fiber 32 is for receiving light. As shown in FIG. 15(c), the optical fiber 31 is connected to branch fibers 31a and 31b at the ends of which light-emitting diodes 33 and 34 with two different wavelengths are provided. At the end of the optical fiber 32, there is provided a photodiode 35. The light-emitting diode 33 emits light of a wavelength 810 nm. The light-emitting diode 34 emits light of a wavelength 950 nm. The wavelength 810 nm is the iso-absorption wavelength at which the molar absorption coefficients of oxy-hemoglobin and reduced (deoxy-) hemoglobin are equal. The wavelength 950 nm is the wavelength at which the difference in molar absorption coefficients between the oxy-hemoglobin and the reduced hemoglobin is large.

The two light-emitting diodes 33 and 34 emit light in a time-divided manner. The light emitted by the light-emitting diodes 33 and 34 is irradiated via the light-emitting optical fiber 31 onto the finger of the subject. The light with which the finger is irradiated is reflected by the finger skin, incident on the light-receiving optical fiber 32, and then detected by the photodiode 35. When the light with which the finger is irradiated is reflected by the finger skin, some of the light penetrates through the skin and into the tissue, and is then absorbed by the hemoglobin in the blood flowing in capillary blood vessels. The measurement data obtained by the photodiode 35 is reflectance R, and the absorbance is approximated by log(1/R). Irradiation is conducted with light of the wavelengths 810 nm and 950 nm, and R is measured for each, and then log(1/R) is calculated, thereby measuring absorbance $A_1$ for wavelength 810 nm and absorbance $A_2$ for wavelength 950 nm.

When the reduced hemoglobin concentration is [Hb], and the oxy-hemoglobin concentration is [HbO$_2$], absorbance A$_1$ and A$_2$ are expressed by the following equations:

$$A_1 = a \times ([Hb] \times A_{Hb}(810 \text{ nm}) + [HbO_2] \times A_{HbO_2}(810 \text{ nm}))$$

$$= a \times ([Hb] + [HbO_2]) \times A_{HbO_2}(810 \text{ nm})$$

$$A_2 = a \times ([Hb] \times A_{Hb}(950 \text{ nm}) + [HbO_2] \times A_{HbO_2}(950 \text{ nm}))$$

$$= a \times ([Hb] + [HbO_2]) \times \left(\left(1 - \frac{[HbO_2]}{[Hb] + [HbO_2]}\right) \times A_{Hb}(950 \text{ nm}) + \frac{[HbO_2]}{[Hb] + [HbO_2]} \times A_{HbO_2}(950 \text{ nm})\right)$$

$A_{Hb}$ (810 nm) and $A_{Hb}$ (950 nm), and $A_{HbO2}$ (810 nm) and $A_{HbO2}$ (950 nm) are molar absorption coefficients of reduced hemoglobin and oxy-hemoglobin, respectively, and are known at the respective wavelengths. Sign a is a proportional coefficient. Based on the above equations, the hemoglobin concentration ([Hb]+[HbO$_2$]) and the hemoglobin oxygen saturation {[HbO$_2$]/([Hb]+[HbO$_2$])} can be determined as follows:

$$[Hb] + [HbO_2] = \frac{A_1}{a \times A_{HbO_2}(810 \text{ nm})}$$

$$\frac{[HbO_2]}{[Hb] + [HbO_2]} = \frac{A_2 \times A_{HbO_2}(810 \text{ nm}) - A_1 \times A_{Hb}(950 \text{ nm})}{A_1 \times (A_{HbO_2}(950 \text{ nm}) - A_{Hb}(950 \text{ nm}))}$$

While in the above example the hemoglobin concentration and hemoglobin oxygen saturation are measured by measuring absorbance at two wavelengths, it is possible to reduce the influence of interfering components and increase measurement accuracy by measuring at three or more wavelengths.

Figure 16:
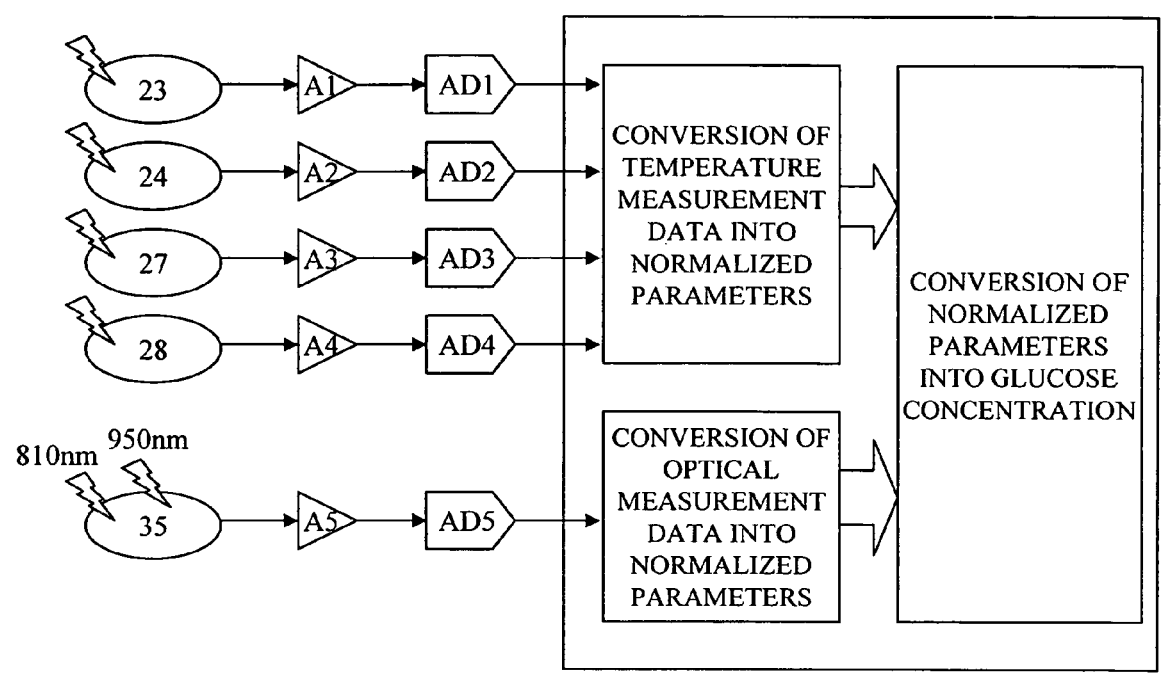
FIG. 16 shows a conceptual chart of the flow of data processing in the apparatus.

FIG. 16 is a conceptual chart illustrating the flow of data processing in the apparatus. The apparatus according to the present example is equipped with five sensors, namely thermistor 23, thermistor 24, pyroelectric detector 27, thermistor 28 and photodiode 35. The photodiode 35 measures the absorbance at wavelength 810 nm and the absorbance at wavelength 950 nm. Thus, six kinds of measurement values are fed to the apparatus.

Five kinds of analog signals are supplied via amplifiers A1 to A5 and digitally converted by analog/digital converters AD1 to AD5. Based on the digitally converted values, parameters $x_i$ (i=1, 2, 3, 4, 5) are calculated. The following are specific descriptions of $x_i$ (where $a_1$ to $a_5$ are proportionality coefficients):

Parameter proportional to heat radiation $$x_1 = a_1 \times (T_3)^4$$

Parameter proportional to heat convection $$x_2 = a_2 \times (T_4 - T_3)$$

Parameter corresponding to hemoglobin concentration $$x_3 = a_3 \left(\frac{A_1}{a \times A_{HbO_2}(810 \text{ nm})}\right)$$

Parameter proportional to hemoglobin oxygen saturation $$x_4 = a_4 \times \left(\frac{A_2 \times A_{HbO_2}(810 \text{ nm}) - A_1 \times A_{Hb}(950 \text{ nm})}{A_1 \times (A_{HbO_2}(950 \text{ nm}) - A_{Hb}(950 \text{ nm}))}\right)$$

Parameter proportional to blood supply volume $$x_5 = a_5 \times \left(\frac{1}{t_{CONT} \times (S_1 - S_2)}\right)$$

Then, normalized parameters are calculated from mean values and standard deviations of parameters $x_i$ obtained for each patient from actual data from large numbers of able-bodied people and diabetic patients. A normalized parameter $X_i$ (where i=1, 2, 3, 4, 5) is calculated from each parameter $x_i$ according to the following equation:

$$X_i = \frac{x_i - \bar{x}_i}{SD(x_i)}$$

where
$x_i$: parameter
$\bar{x}_i$: mean value of the parameter
$SD(x_i)$: standard deviation of the parameter Calculations are conducted to convert the above five normalized parameters into a glucose concentration to be eventually displayed. Programs necessary for computations are stored in the ROM built inside the microprocessor in the apparatus. Memory areas necessary for computations are ensured in a RAM built inside the apparatus. The results of the calculations are displayed on the LCD portion.

The ROM stores, as a constituent element of the program necessary for the computations, a function for determining glucose concentration C in particular. The function is defined as follows. C is expressed by a below-indicated equation (1), where $a_i$ (i=0, 1, 2, 3, 4, 5) is determined from a plurality of pieces of measurement data in advance according to the following procedure:

(1) A multiple regression equation is created that indicates the relationship between the normalized parameter and the glucose concentration C.
(2) Normalized equations (simultaneous equations) relating to the normalized parameter are obtained from an equation obtained by the least-squares method.
(3) Values of coefficient $a_i$ (i=0, 1, 2, 3, 4, 5) are determined from the normalized equation and then substituted into the multiple regression equation.

Initially, the regression equation (1) indicating the relationship between the glucose concentration C and the normalized parameters $X_1$, $X_2$, $X_3$, $X_4$ and $X_5$ is formulated.

$$C = f(X_1, X_2, X_3, X_4, X_5) \quad (1)$$
$$= a_0 + a_1 X_1 + a_2 X_2 + a_3 X_3 + a_4 X_4 + a_5 X_5$$

Then, the least-squares method is employed to obtain a multiple regression equation that would minimize the error with respect to a measured value $C_i$ of glucose concentration according to an enzyme electrode method. When the sum of squares of the residual is D, D is expressed by the following equation (2):

$$D = \sum_{i=1}^{n} d_i^2 \quad (2)$$

$$= \sum_{i=1}^{n} (C_i - f(X_{i1}, X_{i2}, X_{i3}, X_{i4}, X_{i5}))^2$$

$$= \sum_{i=1}^{n} \{C_i - (a_0 + a_1 X_{i1} + a_2 X_{i2} + a_3 X_{i3} + a_4 X_{i4} + a_5 X_{i5})\}^2$$

The sum of squares of the residual D becomes minimum when partial differentiation of equation (2) with respect to $a_0, a_2, \ldots, a_5$ gives zero. Thus, we have the following equations:

$$\frac{\partial D}{\partial a_0} = -2 \sum_{i=1}^{n} \{C_i - (a_0 + a_1 X_{i1} + a_2 X_{i2} + a_3 X_{i3} + a_4 X_{i4} + a_5 X_{i5})\} = 0 \quad (3)$$

$$\frac{\partial D}{\partial a_1} = -2 \sum_{i=1}^{n} X_{i1} \{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_2} = -2 \sum_{i=1}^{n} X_{i2} \{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_3} = -2 \sum_{i=1}^{n} X_{i3} \{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_4} = -2 \sum_{i=1}^{n} X_{i4} \{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_5} = -2 \sum_{i=1}^{n} X_{i5} \{C_i - (a_0 + a_1 X_{i1} + a_2 X_{i2} + a_3 X_{i3} + a_4 X_{i4} + a_5 X_{i5})\} = 0$$

When the mean values of C and $X_1$ to $X_5$ are $C_{mean}$ and $X_{1mean}$ to $X_{5mean}$, respectively, since $X_{imean}=0$ (i=1 to 5), equation (1) yields equation (4) thus:

$$a_0 = C_{mean} - a_1 X_{1mean} - a_2 X_{2mean} - a_3 X_{3mean} - \quad (4)$$

$$a_4 X_{4mean} - a_5 X_{5mean}$$

$$= C_{mean}$$

The variation and covariation between the normalized parameters are expressed by equation (5). Covariation between the normalized parameter $X_i$ (i=1 to 5) and C is expressed by equation (6).

$$S_{ij} = \sum_{k=1}^{n} (X_{ki} - X_{imean})(X_{kj} - X_{jmean}) \quad (5)$$

$$= \sum_{k=1}^{n} X_{ki} X_{kj} \quad (i, j = 1, 2, \ldots 5)$$

$$S_{iC} = \sum_{k=1}^{n} (X_{ki} - X_{imean})(C_k - C_{mean}) \quad (6)$$

$$= \sum_{k=1}^{n} X_{ki} (C_k - C_{mean}) \quad (i = 1, 2, \ldots 5)$$

Substituting equations (4), (5), and (6) into equation (3) and rearranging yields simultaneous equations (normalized equations) (7). Solving equations (7) yields $a_1$ to $a_5$.

$$a_1 S_{11} + a_2 S_{12} + a_3 S_{13} + a_4 S_{14} + a_5 S_{15} = S_{1C}$$

$$a_1 S_{21} + a_2 S_{22} + a_3 S_{23} + a_4 S_{24} + a_5 S_{25} = S_{2C}$$

$$a_1 S_{31} + a_2 S_{32} + a_3 S_{33} + a_4 S_{34} + a_5 S_{35} = S_{3C}$$

$$a_1 S_{41} + a_2 S_{42} + a_3 S_{43} + a_4 S_{44} + a_5 S_{45} = S_{4C}$$

$$a_1 S_{51} + a_2 S_{52} + a_3 S_{53} + a_4 S_{54} + a_5 S_{55} = S_{5C} \quad (7)$$

Constant term $a_0$ is obtained by means of equation (4). The thus obtained $a_i$ (i=0, 1, 2, 3, 4, 5) is stored in ROM at the time of manufacture of the apparatus. In actual measurement using the apparatus, the normalized parameters $X_1$ to $X_5$ obtained from the measured values are substituted into regression equation (1) to calculate the glucose concentration C.

Hereafter, an example of the process of calculating the glucose concentration will be described. The coefficients in equation (1) are determined in advance based on a large quantity of data obtained from able-bodied persons and diabetic patients. The ROM in the microprocessor stores the following formula for the calculation of glucose concentration:

$$C = 99.4 + 18.3 \times X_1 - 20.2 \times X_2 - 23.7 \times X_3 - 22.0 \times X_4 - 25.9 \times X_5$$

$X_1$ to $X_5$ are the results of normalization of parameters $x_1$ to $x_5$. Assuming the distribution of the parameters is normal, 95% of the normalized parameters take on values between −2 and +2.

In an example of measured values for an able-bodied person, substituting normalized parameters $X_1 = -0.06$, $X_2 = +0.04$ and $X_3 = +0.05$, $X_4 = -0.12$ and $X_5 = +0.10$ in the above equation yields C=96 mg/dL. In an example of measured values for a diabetic patient, substituting normalized parameters $X_1 = +1.15$, $X_2 = -1.02$, $X_3 = -0.83$, $X_4 = -0.91$ and $X_5 = -1.24$ in the equation yields C=213

Hereafter, the results of measurement by the conventional enzymatic electrode method and those by the embodiment of the invention will be described. In the enzymatic electrode method, a blood sample is reacted with a reagent and the amount of resultant electrons is measured to determine blood sugar level. When the glucose concentration was 89 mg/dL according to the enzymatic electrode method in an example of measured values for an able-bodied person, substituting the normalized parameters $X_1 = -0.06$, $X_2 = +0.04$, $X_3 = +0.05$, $X_4 = -0.12$ and $X_5 = +0.10$ obtained by measurement at the same time according to the inventive method into the above equation yielded C=96 mg/dL. Further, when the glucose concentration was 238 mg/dL according to the enzymatic electrode method in an example of measurement values for a diabetic patient, substituting the normalized parameters $X_1 = +1.15$, $X_2 = -1.02$, $X_3 = -0.83$, $X_4 = -0.91$ and $X_5 = -1.24$ obtained by measurement at the same time according to the inventive method into the above equation yielded C=213 mg/dL. From the above results, it has been confirmed that the glucose concentration can be accurately determined using the method of the invention.

Figure 17:
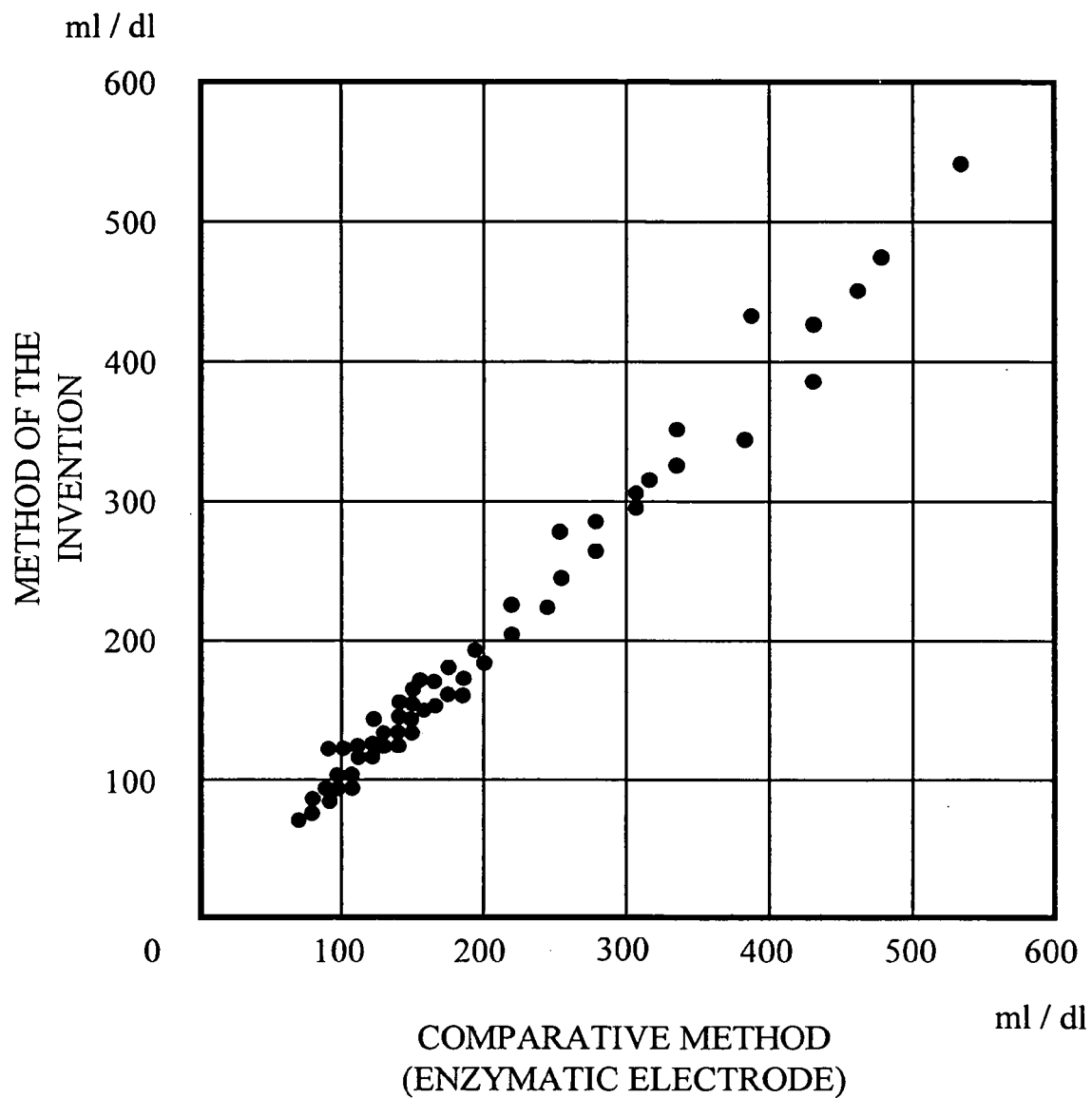
FIG. 17 shows a graph plotting calculated values of glucose concentration according to the invention and measured values of glucose concentration according to the enzymatic electrode method.

FIG. 17 shows a chart plotting on the vertical axis the values of glucose concentration calculated by the inventive method and on the horizontal axis the values of glucose concentration measured by the enzymatic electrode method, based on measurement values obtained from a plurality of patients. A good correlation is obtained by measuring the oxygen supply amount and blood flow volume according to the invention (correlation coefficient=0.9324).

In the above-described embodiment, the parameters relating to blood hemoglobin concentration and blood hemoglobin oxygen saturation are obtained by spectroscopically measuring the hemoglobin in blood. However, the hemoglobin concentration is stable in persons without such symptoms as anemia, bleeding or erythrocytosis. The hemoglobin concentration is normally in the range between 13 to 18 g/dL for males and between 12 to 17 g/dL for females, and the range of variation of hemoglobin concentration from the normal values is 5 to 6%. Further, the weight of the term relating to the blood flow volume in the aforementioned formula for calculating blood sugar level is smaller than other terms. Therefore, the hemoglobin concentration can be treated as a constant without greatly lowering the measurement accuracy. Similarly, the hemoglobin oxygen saturation is stable between 97 to 98% if the person is undergoing aerial respiration at atmospheric pressure, at rest and in a relaxed state. Thus the hemoglobin concentration and the hemoglobin oxygen saturation can be treated as constants, and the oxygen supply amount can be determined from the product of the hemoglobin concentration constant, the hemoglobin oxygen saturation constant and the blood flow volume.

By treating the hemoglobin concentration and hemoglobin oxygen saturation as constants, the sensor arrangement for measuring blood sugar level can be simplified by removing the optical sensors, for example. Further, by eliminating the time necessary for optical measurement and the processing thereof, the procedure for blood sugar level measurement can be accomplished in less time.

Because the hemoglobin oxygen saturation takes on a stable value when at rest, in particular, by treating the hemoglobin concentration and hemoglobin oxygen saturation as constants, the measurement accuracy for blood sugar level measurement when at rest can be increased, and the procedure of blood sugar level measurement can be accomplished in less time. By "when at rest" herein is meant the state in which the test subject has been either sitting on a chair or lying and thus moving little for approximately five minutes.

Hereafter, an embodiment will be described in which the blood hemoglobin concentration and blood hemoglobin oxygen saturation are treated as constants. This embodiment is similar to the above-described embodiment except that the blood hemoglobin concentration and blood hemoglobin oxygen saturation are treated as constants, and therefore the following description mainly concerns the differences from the earlier embodiment.

Figure 18A:
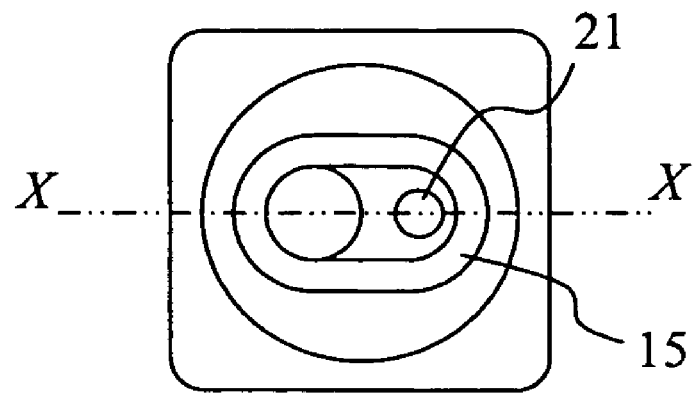
FIG. 18 shows another example of the measuring portion in detail.
Figure 18B:
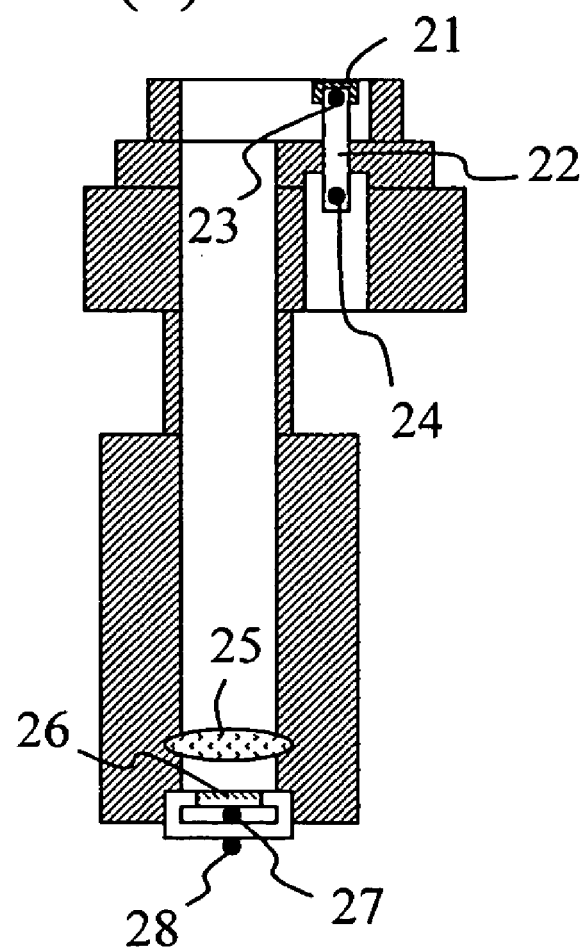

In the present embodiment, the hemoglobin concentration and hemoglobin oxygen saturation shown in FIG. 4 are not measured but treated as constants. Therefore, as shown in FIG. 18, the measurement portion of the present embodiment has the structure of the measurement portion of the earlier embodiment shown in FIG. 15 from which the light sources 33 and 34, photodiode 35 and optical fibers 31 and 32 have been removed. Parameters used in the present embodiment are parameter $x_1$ proportional to heat radiation, parameter $x_2$ related to heat convection, and parameter $x_3$ proportional to the oxygen supply amount (hereafter, parameter proportional to oxygen supply amount will be indicated as $x_3$). From these parameters, normalized parameters are calculated in the manner described above, and a glucose concentration is calculated based on the three normalized parameters $X_i$ (i=1, 2, 3). During data processing, the step "CONVERSION OF OPTICAL MEASUREMENT DATA INTO NORMALIZED PARAMETERS" (see FIG. 16), which is necessary in the previous embodiment, can be omitted.

Figure 19:
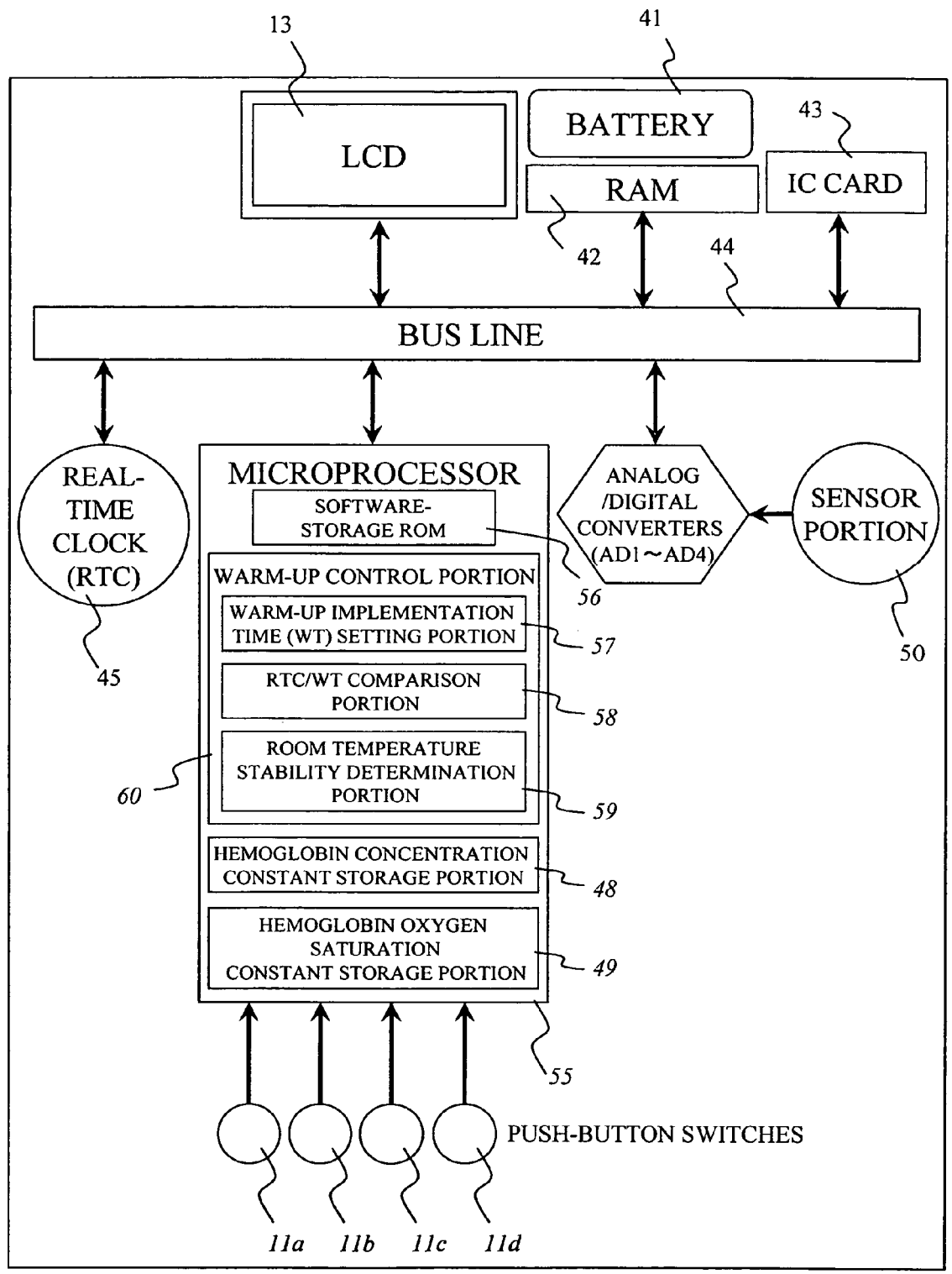
FIG. 19 shows a conceptual chart illustrating data storage locations in the apparatus.

FIG. 19 shows a functional block diagram of the apparatus according to the embodiment. The apparatus runs on battery 41. Signals measured by sensor portion 50 including a temperature sensor are fed to analog/digital converters (AD1 to AD4) provided for individual signals and are converted into digital signals. Analog/digital converters AD1 to AD4, LCD 13 and RAM 42 are peripheral circuits for microprocessor 55. They are accessed by the microprocessor 55 via bus line 44. The push buttons 11a to 11d are connected to the microprocessor 55. The microprocessor 55 includes the ROM for storing software. By pressing the buttons 11a to 11d, external instructions can be entered into the microprocessor 55.

The ROM 56 included in the microprocessor 55 stores a program necessary for computations, i.e., it has the function of an arithmetic unit. The microprocessor 55 further includes a hemoglobin concentration constant storage portion 48 for storing hemoglobin concentration constants, and a hemoglobin oxygen saturation constant storage portion 49 for storing hemoglobin oxygen saturation constants. After the measurement of the finger is finished, the computing program calls optimum constants from the hemoglobin concentration storage portion 48 and hemoglobin oxygen saturation constant storage portion 49 and perform calculations. A memory area necessary for computations is ensured in the RAM 42 similarly incorporated into the apparatus. The result of computations is displayed on the LCD portion. As in the previous embodiment, the microprocessor 55 includes a warm-up control portion 60 consisting of a warm-up implementation time (WT) setting portion 57, a real-time clock (RTC)/WT comparison portion 58, and a room temperature stability determination portion 59.

The ROM stores, as a constituent element of the program necessary for the computations, a function for determining glucose concentration C in particular. The function is defined as follows. C is expressed by a below-indicated equation (8), where $a_i$ (i=0, 1, 2, 3) is determined from a plurality of pieces of measurement data in advance according to the following procedure:

(1) A multiple regression equation is created that indicates the relationship between the normalized parameter and the glucose concentration C.
(2) Normalized equations (simultaneous equations) relating to the normalized parameter are obtained from an equation obtained by the least-squares method.
(3) Values of coefficient $a_i$ (i=0, 1, 2, 3) are determined from the normalized equation and then substituted into the multiple regression equation.

Initially, the regression equation (8) indicating the relationship between the glucose concentration C and the normalized parameters $X_1$, $X_2$ and $X_3$ is formulated.

$$C = f(X_1, X_2, X_3) \qquad (8)$$
$$= a_0 + a_1 X_1 + a_2 X_2 + a_3 X_3$$

Then, the least-squares method is employed to obtain a multiple regression equation that would minimize the error with respect to a measured value $C_i$ of glucose concentration according to an enzyme electrode method. When the sum of squares of the residual is D, D is expressed by the following equation (9):

$$D = \sum_{i=1}^{n} d_i^2 \qquad (9)$$

$$= \sum_{i=1}^{n} (C_i - f(X_{i1}, X_{i2}, X_{i3}))^2$$

$$= \sum_{i=1}^{n} \{C_i - (a_0 + a_1 X_{i1} + a_2 X_{i2} + a_3 X_{i3})\}^2$$

The sum of squares of the residual D becomes minimum when partial differentiation of equation (9) with respect to $a_0$ to $a_3$ gives zero. Thus, we have the following equations:

$$\frac{\partial D}{\partial a_0} = -2\sum_{i=1}^{n} \{C_i - (a_0 + a_1 X_{i1} + a_2 X_{i2} + a_3 X_{i3})\} \qquad (10)$$
$$= 0$$

$$\frac{\partial D}{\partial a_1} = -2\sum_{i=1}^{n} X_{i1}\{C_i - (a_0 + a_1 X_{i1} + a_2 X_{i2} + a_3 X_{i3})\}$$
$$= 0$$

$$\frac{\partial D}{\partial a_2} = -2\sum_{i=1}^{n} X_{i2}\{C_i - (a_0 + a_1 X_{i1} + a_2 X_{i2} + a_3 X_{i3})\}$$
$$= 0$$

$$\frac{\partial D}{\partial a_3} = -2\sum_{i=1}^{n} X_{i3}\{C_i - (a_0 + a_1 X_{i1} + a_2 X_{i2} + a_3 X_{i3})\}$$
$$= 0$$

When the mean values of C and $X_1$ to $X_3$ are $C_{mean}$ and $X_{1mean}$ to $X_{3mean}$, respectively, since $X_{imean}=0$ (i=1 to 3), equation (8) yields equation (11) thus:

$$a_0 = C_{mean} - a_1 X_{1mean} - a_2 X_{2mean} - a_3 X_{3mean} \qquad (11)$$
$$= C_{mean}$$

The variation and covariation between the normalized parameters are expressed by equation (12). Covariation between the normalized parameter $X_i$ (i=1 to 3) and C is expressed by equation (13).

$$S_{ij} = \sum_{k=1}^{n} (X_{ki} - X_{imean})(X_{kj} - X_{jmean}) \qquad (12)$$
$$= \sum_{k=1}^{n} X_{ki} X_{kj} \qquad (i, j = 1, 2, 3)$$

$$S_{iC} = \sum_{k=1}^{n} (X_{ki} - X_{imean})(C_k - C_{mean}) \qquad (13)$$
$$= \sum_{k=1}^{n} X_{ki}(C_k - C_{mean}) \qquad (i = 1, 2, 3)$$

Substituting equations (11), (12), and (13) into equation (10) and rearranging yields simultaneous equations (normalized equations) (14). Solving equations (14) yields $a_1$ to $a_3$.

$$a_1 S_{11} + a_2 S_{12} + a_3 S_{13} = S_{1C}$$

$$a_1 S_{21} + a_2 S_{22} + a_3 S_{23} = S_{2C}$$

$$a_1 S_{31} + a_2 S_{32} + a_3 S_{33} = S_{3C} \qquad (14)$$

Constant term $a_0$ is obtained by means of equation (11). The thus obtained $a_i$ (i=0, 1, 2, 3) is stored in ROM at the time of manufacture of the apparatus. In actual measurement using the apparatus, the normalized parameters $X_1$ to $X_3$ obtained from the measured values are substituted into regression equation (8) to calculate the glucose concentration C.

Hereafter, an example of the process of calculating the glucose concentration will be described. The coefficients in equation (8) are determined in advance based on a large quantity of data obtained from able-bodied persons and diabetic patients. The ROM in the microprocessor stores the following formula for the calculation of glucose concentration:

$$C = 101.7 + 25.8 \times X_1 - 23.2 \times X_2 - 12.9 \times X_3$$

$X_1$ to $X_3$ are the results of normalization of parameters $x_1$ to $x_3$. Assuming the distribution of the parameters is normal, 95% of the normalized parameters take on values between −2 and +2.

In an example of measured values for an able-bodied person, substituting normalized parameters $X_1$=−0.06, $X_2$=+0.04 and $X_3$=+0.10 in the above equation yields C=101 mg/dL. In an example of measured values for a diabetic patient, substituting normalized parameters $X_1$=+1.35, $X_2$=−1.22 and $X_3$=−1.24 in the equation yields C=181 mg/dL. In the above equation, the hemoglobin concentration and hemoglobin oxygen saturation are rendered into constants of 15 g/dL and 97%, respectively.

Hereafter, the results of measurement by the conventional enzymatic electrode method and those by the embodiment of the invention will be described. In the enzymatic electrode method, a blood sample is reacted with a reagent and the amount of resultant electrons is measured to determine the blood sugar level. When the glucose concentration was 93 mg/dL according to the enzymatic electrode method in an example of measured values for an able-bodied person, substituting normalized parameters $X_1$=−0.06, $X_2$=+0.04 and $X_3$=+0.10 obtained by measurement at the same time according to the inventive method into the above equation yielded C=101 mg/dL. Further, when the glucose concentration was 208 mg/dL according to the enzymatic electrode method in an example of measurement values for a diabetic patient, substituting the normalized parameters $X_1$=+1.35, $X_2$=−1.22 and $X_3$=−1.24 obtained by measurement at the same time according to the inventive method into the above equation yielded C=181 mg/dL. Although the calculation results indicate an error of about 13%, this level of accuracy is considered sufficient because normally errors between 15% and 20% are considered acceptable in blood sugar level measuring apparatuses in general. Thus, it has been confirmed that the method of the invention can allow glucose concentrations to be determined with high accuracy.

Figure 20:
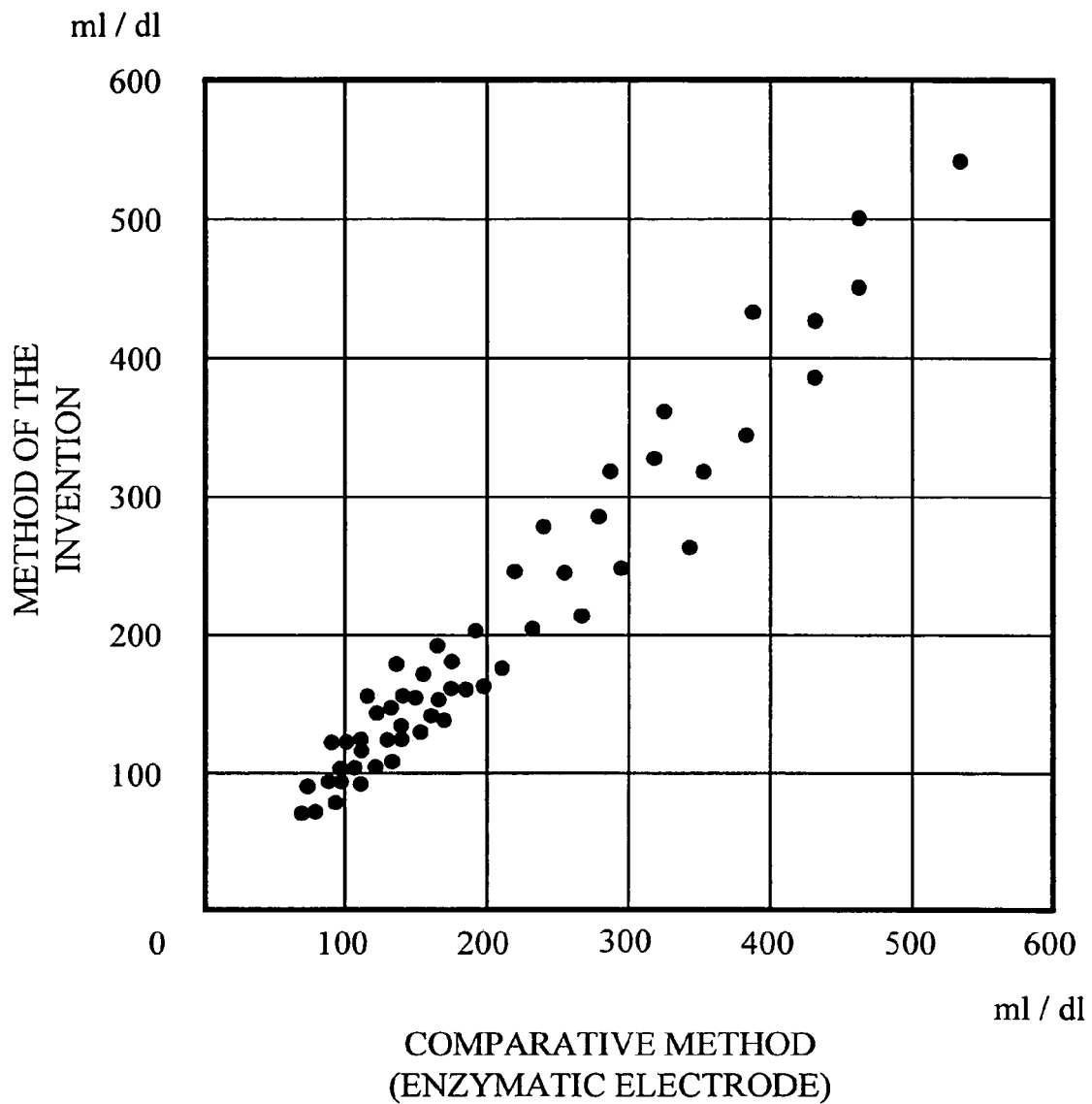
FIG. 20 shows a graph plotting calculated values of glucose concentration according to the invention and measured values of glucose concentration according to the enzymatic electrode method.

FIG. 20 shows a chart plotting on the vertical axis the values of glucose concentration calculated by the inventive method and on the horizontal axis the values of glucose concentration measured by the enzymatic electrode method, based on measurement values obtained from a plurality of patients. A good correlation is obtained by measuring according to the invention (correlation coefficient=0.8932).

What is claimed is:

1. A blood sugar level measuring apparatus comprising:
   a heat amount measurement portion for measuring a plurality of temperatures derived from a body surface and obtaining information used for calculating the amount of heat transferred by convection and the amount of heat transferred by radiation, both related to the dissipation of heat from said body surface;
   an oxygen amount measuring portion for obtaining information about blood oxygen amount;
   a storage portion for storing a relationship between parameters corresponding to said plurality of temperatures and blood oxygen amount and blood sugar levels;
   a calculating portion which converts a plurality of measurement values fed from said heat amount measuring portion and said oxygen amount measurement portion into said parameters, and which computes a blood sugar level by applying said parameters to said relationship stored in said storage portion;
   a display portion for displaying the result calculated by said calculating portion; and
   a warm-up control portion for conducting a warm-up, wherein
   said oxygen-amount measuring portion comprises a blood flow volume measuring portion for obtaining information about the volume of blood flow, and an optical measuring portion for obtaining hemoglobin concentration and hemoglobin oxygen saturation in blood,
   said blood flow volume measuring portion comprises a body-surface contact portion, a first temperature detector disposed adjacent to said body-surface contact portion, a second temperature detector for detecting the temperature at a position spaced away from said body-surface contact portion, and a heat-conducting member connecting said body-surface contact portion and said second temperature detector, and
   said warm-up control portion checks whether the temperature measured by said heat amount measuring portion or said blood flow volume measuring portion during said warm-up is in a predetermined temperature range.

2. The blood sugar level measuring apparatus according to claim 1, wherein said warm-up control portion checks the temperature measured by said first temperature detector during said warm-up.

3. The blood sugar level measuring apparatus according to claim 1, wherein said warm-up control portion checks the temperature measured by said second temperature detector during said warm-up.

4. The blood sugar level measuring apparatus according to claim 1, wherein said heat amount measuring portion comprises a third temperature detector for measuring an ambient temperature, and wherein said warm-up control portion checks the temperature measured by said third temperature detector during said warm-up.

5. The blood sugar level measuring apparatus according to claim 1, wherein said warm-up control portion checks whether the temperature measured during said warm-up is in the range between 10° C. and 30° C.

6. The blood sugar level measuring apparatus according to claim 1, wherein said warm-up control portion checks said temperature during said warm-up at predetermined time intervals.

7. The blood sugar level measuring apparatus according to claim 1, wherein said warm-up control portion compares the temperatures measured during said warm-up at predetermined time intervals to check checks whether the difference between two temperature measurement values is in a predetermined range.

8. A blood sugar level measuring apparatus comprising:
   an ambient temperature measuring device for measuring ambient temperature;
   a body-surface contact portion to which a body surface is brought into contact;
   an adjacent-temperature detector disposed adjacent to said body-surface contact portion;
   a radiant heat detector for measuring radiant heat from said body surface;
   a heat conducting member disposed in contact with said body-surface contact portion;
   an indirect-temperature detector disposed at a position that is adjacent to said heat conducting member and that is spaced apart from said body-surface contact portion, said indirect-temperature detector measuring temperature at the position spaced apart from said body-surface contact portion;
   a light source for irradiating said body-surface contact portion with light of at least two different wavelengths;
   a photodetector;
   a converter for converting outputs from said adjacent-temperature detector, said indirect-temperature detector, said ambient temperature detector, said radiant heat detector and said photodetector, into parameters;
   a calculating portion in which a relationship between said parameters and blood sugar levels is stored in advance, said calculating portion including a processing portion for calculating a blood sugar level by applying said parameters to said relationship;
   a display portion for displaying the result outputted from said calculating portion; and
   a warm-up control portion for conducting a warm-up, wherein
   said warm-up control portion checks whether the temperature measured by said ambient temperature measuring device, said adjacent-temperature detector, or said indirect-temperature detector during said warm-up is in a predetermined temperature range.

9. The blood sugar level measuring apparatus according to claim 8, wherein said warm-up control portion checks whether the temperature measured during said warm-up is in the range between 10° C. and 30° C.

10. The blood sugar level measuring apparatus according to claim 8, wherein said warm-up control portion checks said temperature during said warm-up at predetermined time intervals.

11. The blood sugar level measuring apparatus according to claim 8, wherein said warm-up control portion compares said temperatures measured during said warm-up at predetermined time intervals checks whether the difference between two temperature measurement values is in a predetermined range.

12. A blood sugar level measuring apparatus comprising:
   an ambient temperature measuring device for measuring ambient temperature;
   a body-surface contact portion to which a body surface is brought into contact;
   an adjacent-temperature detector disposed adjacent to said body-surface contact portion;
   a radiant heat detector for measuring radiant heat from said body surface;
   a heat conducting member disposed in contact with said body-surface contact portion;

an indirect-temperature detector disposed at a position that is adjacent to said heat conducting member and that is spaced apart from said body-surface contact portion, said indirect-temperature detector measuring temperature at the position spaced apart from said body-surface contact portion;

a storage portion where information about blood hemoglobin concentration and blood hemoglobin oxygen saturation is stored;

a converter for converting outputs from said adjacent-temperature detector, said indirect-temperature detector, said ambient temperature measuring device and said radiant heat detector, into a plurality of parameters;

a calculating portion in which a relationship between said parameters and blood sugar levels is stored in advance, said calculating portion including a processing portion for calculating a blood sugar level by applying said parameters to said relationship;

a display portion for displaying the result outputted from said calculating portion; and a warm-up control portion for conducting a warm-up, wherein said warm-up control portion checks whether the temperature measured by said ambient temperature measuring device, said adjacent-temperature detector, or said indirect-temperature detector during said warm-up is in a predetermined temperature range.

13. The blood sugar level measuring apparatus according to claim 12, wherein said warm-up control portion checks whether said temperature measured during said warm-up is in the range between 10° C. and 30° C.

14. The blood sugar level measuring apparatus according to claim 12, wherein said warm-up control portion checks said temperature during said warm-up at predetermined time intervals.

15. The blood sugar level measuring apparatus according to claim 12, wherein said warm-up control portion compares the temperatures measured during said warm-up at predetermined time intervals to checks whether the difference between two temperature measurement values is in a predetermined range.

* * * * *